(12) United States Patent
Naveena-Chandran

(10) Patent No.: US 12,241,360 B2
(45) Date of Patent: Mar. 4, 2025

(54) DOWNHOLE ROTARY CORE ANALYSIS USING IMAGING, PULSE NEUTRON, AND NUCLEAR MAGNETIC RESONANCE

(71) Applicant: Halliburton Energy Services, Inc., Houston, TX (US)

(72) Inventor: Rohin Naveena-Chandran, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 18/433,056

(22) Filed: Feb. 5, 2024

(65) Prior Publication Data

US 2024/0175346 A1  May 30, 2024

Related U.S. Application Data

(63) Continuation of application No. 17/854,202, filed on Jun. 30, 2022, now Pat. No. 11,927,089.

(60) Provisional application No. 63/253,782, filed on Oct. 8, 2021.

(51) Int. Cl.
*E21B 47/002* (2012.01)
*E21B 49/06* (2006.01)
*E21B 49/08* (2006.01)
*G01N 33/24* (2006.01)

(52) U.S. Cl.
CPC ............ *E21B 47/002* (2020.05); *E21B 49/06* (2013.01); *G01N 33/24* (2013.01)

(58) Field of Classification Search
CPC ........ E21B 49/06; E21B 49/08; E21B 49/083; E21B 25/02
See application file for complete search history.

(56) References Cited

U.S. PATENT DOCUMENTS

| | | | | |
|---|---|---|---|---|
| 2,044,057 A | * | 6/1936 | Burt | E21B 25/10 |
| | | | | 175/249 |
| 2,260,562 A | * | 10/1941 | Dillon | E21B 47/026 |
| | | | | 324/377 |
| 2,628,816 A | * | 2/1953 | Mahan | E21B 25/16 |
| | | | | 175/248 |
| 2,650,069 A | * | 8/1953 | Rand | E21B 25/18 |
| | | | | 175/6 |

(Continued)

FOREIGN PATENT DOCUMENTS

| | | |
|---|---|---|
| CN | 107109915 | 8/2017 |
| JP | 2002-227580 | 8/2002 |

(Continued)

OTHER PUBLICATIONS

International Search Report and Written Opinion for Application No. PCT/US2022/036529, dated Oct. 18, 2022.

(Continued)

*Primary Examiner* — Jennifer H Gay
(74) *Attorney, Agent, or Firm* — John Wustenberg; C. Tumey Law Group PLLC

(57) ABSTRACT

In general, in one aspect, embodiments relate to a downhole tool that includes a coring module for obtaining at least one rotary core sample from a formation, and a core marker module for marking the at least one rotary core sample with earth coordinates, where the coring module is separate from the core marker module.

20 Claims, 18 Drawing Sheets

(56) References Cited

U.S. PATENT DOCUMENTS

| | | | | |
|---|---|---|---|---|
| 3,596,511 | A * | 8/1971 | Hart | E21B 49/06 318/434 |
| 4,449,593 | A * | 5/1984 | Jageler | E21B 49/06 175/58 |
| 4,714,119 | A * | 12/1987 | Hebert | E21B 49/06 175/58 |
| 5,310,013 | A * | 5/1994 | Kishino | E21B 25/16 175/58 |
| 7,293,715 | B2 * | 11/2007 | Bargach | B01L 3/545 235/375 |
| 7,431,107 | B2 * | 10/2008 | Hill | E21B 49/06 175/246 |
| 7,500,388 | B2 * | 3/2009 | Fujisawa | E21B 49/06 73/152.11 |
| 7,748,265 | B2 * | 7/2010 | Reid | E21B 49/081 73/152.09 |
| 8,061,446 | B2 * | 11/2011 | Reid, Jr. | E21B 49/06 175/58 |
| 8,210,284 | B2 * | 7/2012 | Buchanan | E21B 25/16 166/100 |
| 8,292,004 | B2 * | 10/2012 | Buchanan | E21B 49/06 175/58 |
| 8,430,186 | B2 * | 4/2013 | Reid, Jr. | E21B 25/10 175/239 |
| 8,619,501 | B2 * | 12/2013 | Garcia-Osuna | G01N 29/07 73/152.11 |
| 8,684,110 | B2 * | 4/2014 | Reid, Jr. | E21B 25/10 175/239 |
| 9,051,804 | B2 * | 6/2015 | Reid, Jr. | E21B 25/10 |
| 9,097,102 | B2 * | 8/2015 | Ward | E21B 10/02 |
| 9,146,200 | B2 * | 9/2015 | Zarra | G01N 23/046 |
| 9,359,891 | B2 * | 6/2016 | Galvan-Sanchez | E21B 49/10 |
| 9,541,670 | B2 * | 1/2017 | Groves | G01T 7/005 |
| 9,689,256 | B2 * | 6/2017 | Tevis | E21B 49/06 |
| 9,874,063 | B2 * | 1/2018 | Arian | E21B 25/00 |
| 10,221,684 | B2 * | 3/2019 | Westacott | G01V 1/306 |
| 10,550,655 | B2 * | 2/2020 | Jones | E21B 49/06 |
| 11,187,079 | B2 * | 11/2021 | Van Zuilekom | E21B 49/06 |
| 11,686,876 | B2 * | 6/2023 | Mezghani | G01V 3/38 175/50 |
| 11,927,089 | B2 * | 3/2024 | Naveena-Chandran | G01V 3/32 |
| 2004/0140126 | A1 * | 7/2004 | Hill | E21B 49/06 175/58 |
| 2006/0131376 | A1 * | 6/2006 | Bargach | E21B 49/06 702/6 |
| 2007/0137894 | A1 * | 6/2007 | Fujisawa | E21B 49/06 175/58 |
| 2008/0066534 | A1 * | 3/2008 | Reid | E21B 49/081 73/152.09 |
| 2009/0114447 | A1 * | 5/2009 | Reid, Jr. | E21B 25/00 175/58 |
| 2010/0282515 | A1 * | 11/2010 | Reid, Jr. | E21B 49/06 175/239 |
| 2011/0094801 | A1 * | 4/2011 | Buchanan | E21B 4/04 175/249 |
| 2011/0242938 | A1 * | 10/2011 | Garcia-Osuna | G01N 29/07 367/89 |
| 2011/0284289 | A1 * | 11/2011 | Buchanan | E21B 49/06 175/244 |
| 2013/0081879 | A1 * | 4/2013 | Ward | E21B 10/02 175/94 |
| 2013/0233622 | A1 * | 9/2013 | Reid | E21B 25/10 175/58 |
| 2013/0308753 | A1 * | 11/2013 | Groves | G01T 7/005 378/54 |
| 2013/0311099 | A1 | 11/2013 | Eyuboglu et al. | |
| 2014/0102794 | A1 * | 4/2014 | Tevis | E21B 47/024 33/304 |
| 2014/0131033 | A1 * | 5/2014 | Galvan-Sanchez | E21B 49/06 166/250.01 |
| 2014/0209385 | A1 * | 7/2014 | Reid, Jr. | E21B 25/10 175/58 |
| 2014/0328454 | A1 * | 11/2014 | Zarra | G01N 33/24 378/17 |
| 2014/0367086 | A1 * | 12/2014 | Arian | E21B 25/08 166/69 |
| 2015/0315902 | A1 * | 11/2015 | Beach | E21B 47/024 175/45 |
| 2016/0010455 | A1 | 1/2016 | Naveena-Chandran et al. | |
| 2016/0123096 | A1 * | 5/2016 | Mathieson | E21C 41/16 175/50 |
| 2017/0122050 | A1 * | 5/2017 | McLeod | E21B 25/005 |
| 2017/0159429 | A1 * | 6/2017 | Massey | E21B 49/06 |
| 2018/0051559 | A1 * | 2/2018 | Westacott | E21B 49/06 |
| 2018/0245415 | A1 * | 8/2018 | Jones | E21B 47/07 |
| 2018/0371904 | A1 * | 12/2018 | Van Zuilekom | E21B 49/06 |
| 2019/0040735 | A1 * | 2/2019 | McLeod | E21B 47/024 |
| 2019/0145252 | A1 | 5/2019 | Naveena-Chandran | |
| 2021/0123344 | A1 * | 4/2021 | Westacott | G01N 33/0016 |
| 2021/0238999 | A1 | 8/2021 | Naveena-Chandran et al. | |
| 2021/0255353 | A1 * | 8/2021 | Mezghani | G01N 35/00871 |
| 2021/0381315 | A1 * | 12/2021 | Allen | E21B 25/04 |
| 2022/0074302 | A1 * | 3/2022 | Van Zuilekom | E21B 49/06 |
| 2022/0333453 | A1 * | 10/2022 | McElhinney | E21B 47/006 |
| 2023/0112374 | A1 * | 4/2023 | Naveena-Chandran | G01N 33/24 175/40 |
| 2024/0175346 | A1 * | 5/2024 | Naveena-Chandran | E21B 49/06 |

FOREIGN PATENT DOCUMENTS

| | | | | |
|---|---|---|---|---|
| NO | 165213 | | 10/1990 | |
| NO | 20170322 | A1 * | 5/2017 | E21B 25/16 |
| WO | 2011146014 | | 11/2011 | |
| WO | 2016-186626 | | 11/2016 | |
| WO | WO-2017176127 | A1 * | 10/2017 | E21B 17/06 |

OTHER PUBLICATIONS

Office Action Summary for U.S. Appl. No. 17/854,202 dated Aug. 1, 2023.

Final Office Action Summary for U.S. Appl. No. 17/854,202 dated Nov. 6, 2023.

Notice of Allowance for U.S. Appl. No. 17/854,202 dated Jan. 18, 2024.

* cited by examiner

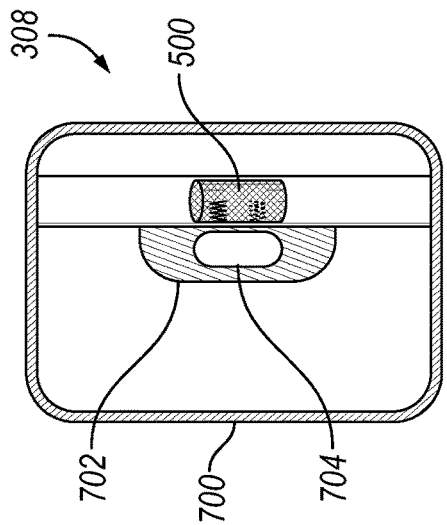
FIG. 7
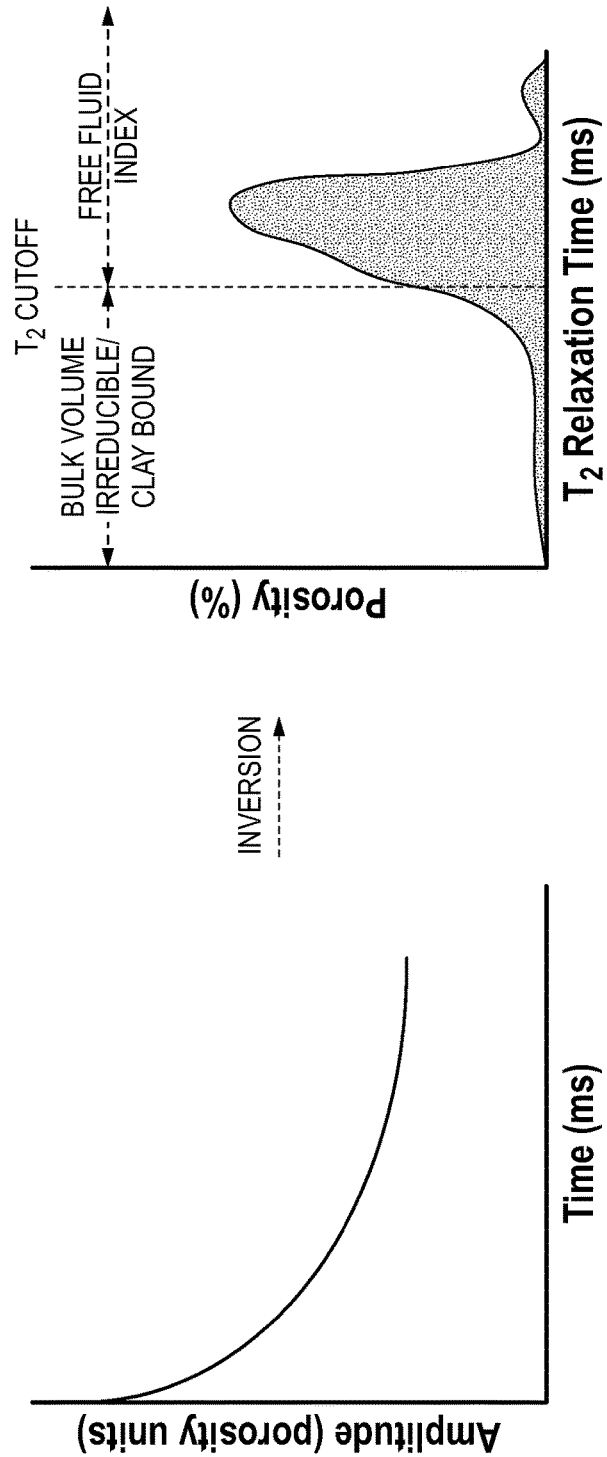
FIG. 8B
FIG. 8A

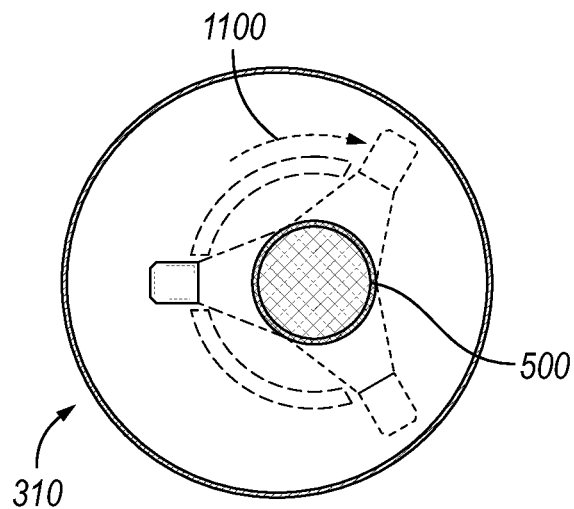
FIG. 12
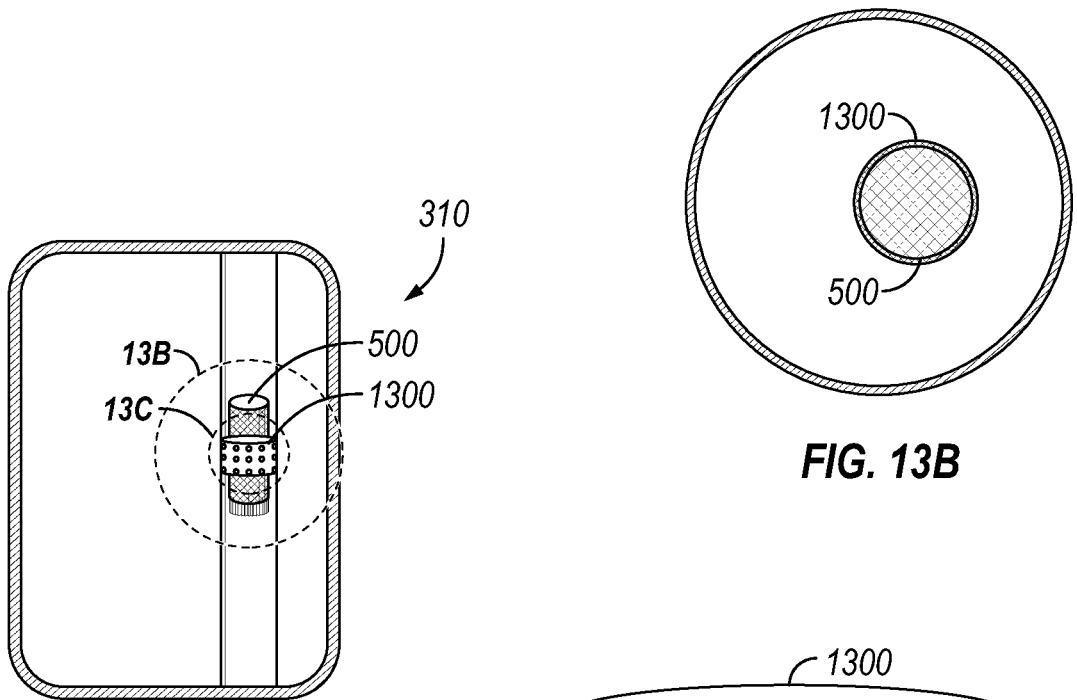
FIG. 13B
FIG. 13A
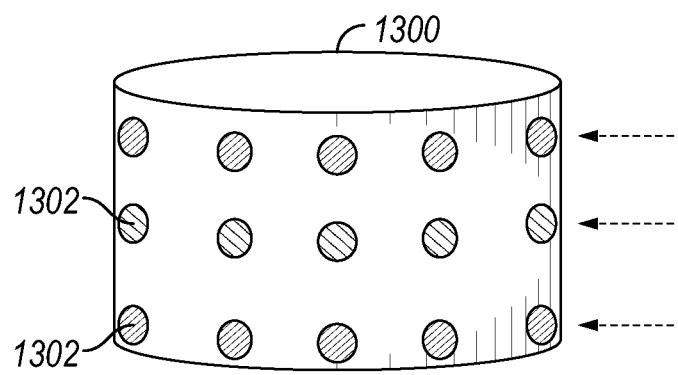
FIG. 13C

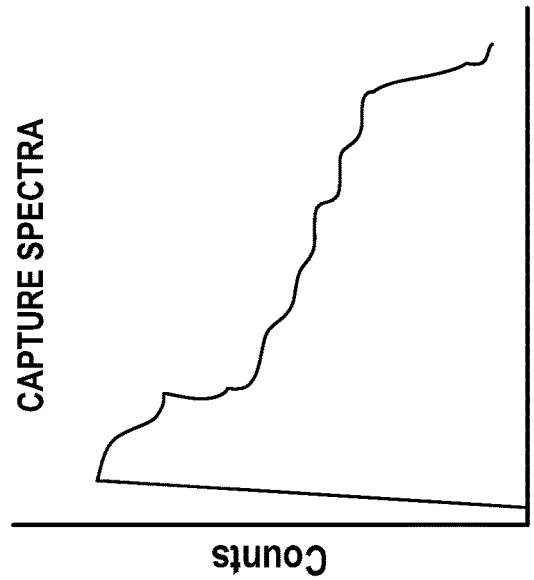
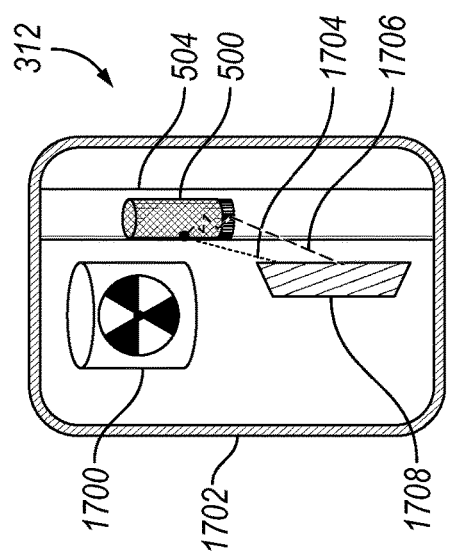
FIG. 17A
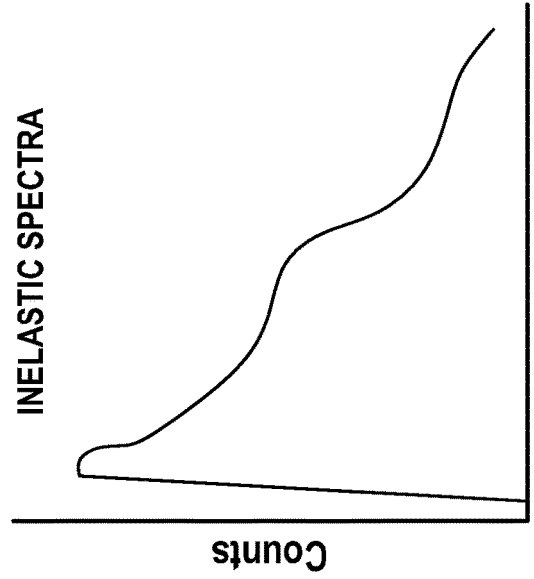

DOWNHOLE ROTARY CORE ANALYSIS USING IMAGING, PULSE NEUTRON, AND NUCLEAR MAGNETIC RESONANCE

CROSS REFERENCE TO RELATED APPLICATIONS

This is a continuation of U.S. patent application Ser. No. 17/854,202 filed Jun. 30, 2022, which claims priority to U.S. Provisional Patent Application No. 63/253,782 filed Oct. 8, 2021, the entire disclosures of which are incorporated herein by reference.

BACKGROUND

During oil and gas exploration, many types of information may be collected and analyzed. The information may be used to determine the quantity and quality of hydrocarbons in a reservoir and to develop or modify strategies for hydrocarbon production. For instance, the information may be used for reservoir evaluation, flow assurance, reservoir stimulation, facility enhancement, production enhancement strategies, and reserve estimation.

One technique for collecting relevant information involves obtaining and analyzing rotary core samples from a reservoir of interest. There are a variety of different tools that may be used to obtain the rotary core samples from a subterranean formation. Conventional analysis has required transfer of the rotary core samples to a laboratory for analysis.

Within Wireline Rotary Coring, there currently is no method in the industry available to analyze properties of a rotary core downhole after a core is acquired and stored. This poses a challenge to make critical decisions that pend post analysis of a laboratory, which may take weeks after the core is recovered. Furthermore, the analysis of cores downhole may reveal data of the wellbore and reservoir that may impact immediate completion plans of the wellbore and field development plans. Within operations, there is no method to see the core integrity after it is recovered. This decreases efficiency to optimize coring programs by being able to select critical coring points by verifying data per wireline logs.

BRIEF DESCRIPTION OF THE DRAWINGS

These drawings illustrate certain aspects of some of the embodiments of the present invention, and should not be used to limit or define the invention:

FIG. 7 illustrate a core nuclear magnetic resonance (NMR) module;

FIGS. 8A and 8B are graphs that illustrate that the amount of time taken to relax is an indication of pore size and fluid inside the pore;

FIG. 12 illustrates another example of the core imaging analysis module;

FIGS. 13A-13C illustrate another example of the core imaging analysis module;

FIG. 17A illustrates a core pulse neutron analysis module;

FIGS. 17B and 17C are graphs that illustrate inelastic spectra measurements;

DETAILED DESCRIPTION

Downhole rotary coring is a downhole operation that may be used for formation evaluation, asset decisions, and operational decisions. Discussed below are methods and system for a device that is attached to a rotary coring tool to analyze the core via Microresistivity, Ultrasonic, Computed Tomography (CT), Pulsed Neutron Analysis, and Nuclear Magnetic Resonance (NMR) to provide an analysis directly after acquisition of the core and all under reservoir pressure and temperature conditions. The results of which may affect the petrophysical analysis, wellbore completions program and field development of a reservoir.

Figure 1:
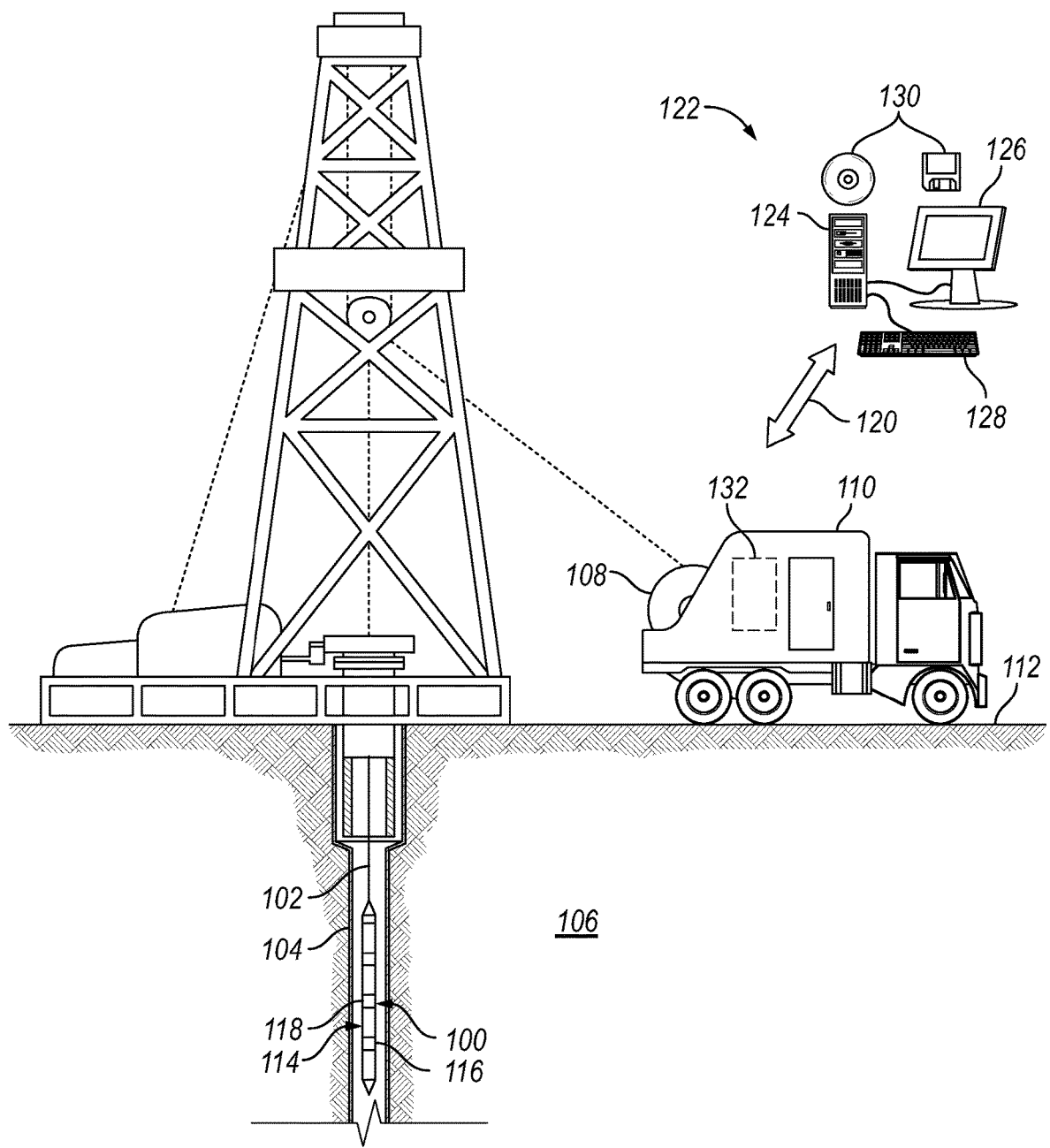
FIG. 1 is a schematic diagram of an example downhole formation rotary coring tool on a wireline.

FIG. 1 is a schematic diagram of downhole formation rotary coring tool 100 on a conveyance 102. As illustrated, wellbore 104 may extend through subterranean formation 106. As illustrated, wellbore 104 may extend through subterranean formation 106. While wellbore 104 is shown extending generally vertically into the subterranean formation 106, the principles described herein are also applicable to wellbores that extend at an angle through the subterranean formation 106, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a hoist 108 may be used to run downhole formation rotary coring tool 100 into wellbore 104. Hoist 108 may be disposed on a vehicle 110. Hoist 108 may be used, for example, to raise and lower conveyance 102 in wellbore 104. While hoist 108 is shown on vehicle 110, it should be understood that conveyance 102 may alternatively be disposed from a hoist 108 that is installed at surface 112 instead of being located on vehicle 110. Downhole formation rotary coring tool 100 may be suspended in wellbore 104 on conveyance 102. Other conveyance types may be used for conveying downhole formation rotary coring tool 100 into wellbore 104, including coiled tubing and wired drill pipe, conventional drill pipe for example. Downhole formation rotary coring tool 100 may comprise a tool body 114, which may be elongated as shown on FIG. 1. Tool body 114 may be any suitable material, including without limitation titanium, stainless steel, alloys, plastic, combinations thereof, and the like. Downhole formation rotary coring tool 100 may further include one or more sensors 116 for measuring properties of a core sample, a reservoir fluid, wellbore 104, subterranean formation 106, and/or the like. In examples, downhole formation rotary coring tool 100 may also include one or more formation analysis modules 118, which may be operable to process information regarding core sample, as described below. The downhole formation rotary coring tool 100 may be used to collect rotary core samples from subterranean formation 106 and may obtain and separately store different rotary core samples from subterrancan formation 106.

In examples, one or more formation analysis modules 118 may comprise at least one a sensor that may continuously monitor a rotary core sample. Such sensors include optical sensors, acoustic sensors, electromagnetic sensors, conductivity sensors, resistivity sensors, selective electrodes, density sensors, mass sensors, thermal sensors, chromatography sensors, viscosity sensors, bubble point sensors, fluid compressibility sensors, flow rate sensors. Sensors may measure a contrast between drilling fluid filtrate properties and formation fluid properties, and formation geology and rock properties. Formation analysis module 118 may be operable to derive properties and characterize the rotary core sample. By way of example, formation analysis module 118 may measure absorption, transmittance, or reflectance spectra and translate such measurements into component concentrations of the rotary core sample, which may be lumped component concentrations, as described above. Transmittance and Reflectance may be measured with the Computed Tomography (CT) module. In examples a CT module may be computed from an X-ray source. Absorption may be measured from the Pulsed Neutron module that measures the amount of gamma rays absorbed by the rock sample.

Formation analysis module 118 may also measure gas-to-oil ratio, fluid composition, water cut, live fluid density, live fluid viscosity, formation pressure, and formation temperature. Formation analysis module 118 may also be operable to determine fluid properties within the rotary core sample and may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, formation analysis module 118 may include random access memory (RAM), one or more processing units, such as a central processing unit (CPU), or hardware or software control logic, ROM, and/or other types of nonvolatile memory.

Any suitable technique may be used for transmitting phase signals from the downhole formation rotary coring tool 100 to surface 112. As illustrated, a communication link 120 (which may be wired or wireless, for example) may be provided that may transmit data from downhole formation rotary coring tool 100 to an information handling system 122 at surface 112. Information handling system 122 may include a processing unit 124, a monitor 126, an input device 128 (e.g., keyboard, mouse, etc.), and/or computer media 130 (e.g., optical disks, magnetic disks) that can store code representative of the methods described herein. The information handling system 122 may act as a data acquisition system and possibly a data processing system that analyzes information from downhole formation rotary coring tool 100. For example, information handling system 122 may process the information from downhole formation rotary coring tool 100 for determination of fluid contamination. Information handling system 122 may also determine additional properties of the rotary core sample. This processing may occur at surface 112 in real-time. Alternatively, the processing may occur downhole hole or at surface 112 or another location after recovery of downhole formation rotary coring tool 100 from wellbore 104. Alternatively, the processing may be performed by an information handling system in wellbore 104, such as within one or more analysis modules 118. The resultant measurements may then be transmitted to surface 112, for example, in real-time. Real time may be defined within any range comprising 0.01 seconds to 0.1 seconds, 0.1 seconds to 1 second, 1 second to 1 minute, 1 minute to 1 hour, 1 hour to 4 hours, or any combination of ranges provided.

Figure 2:
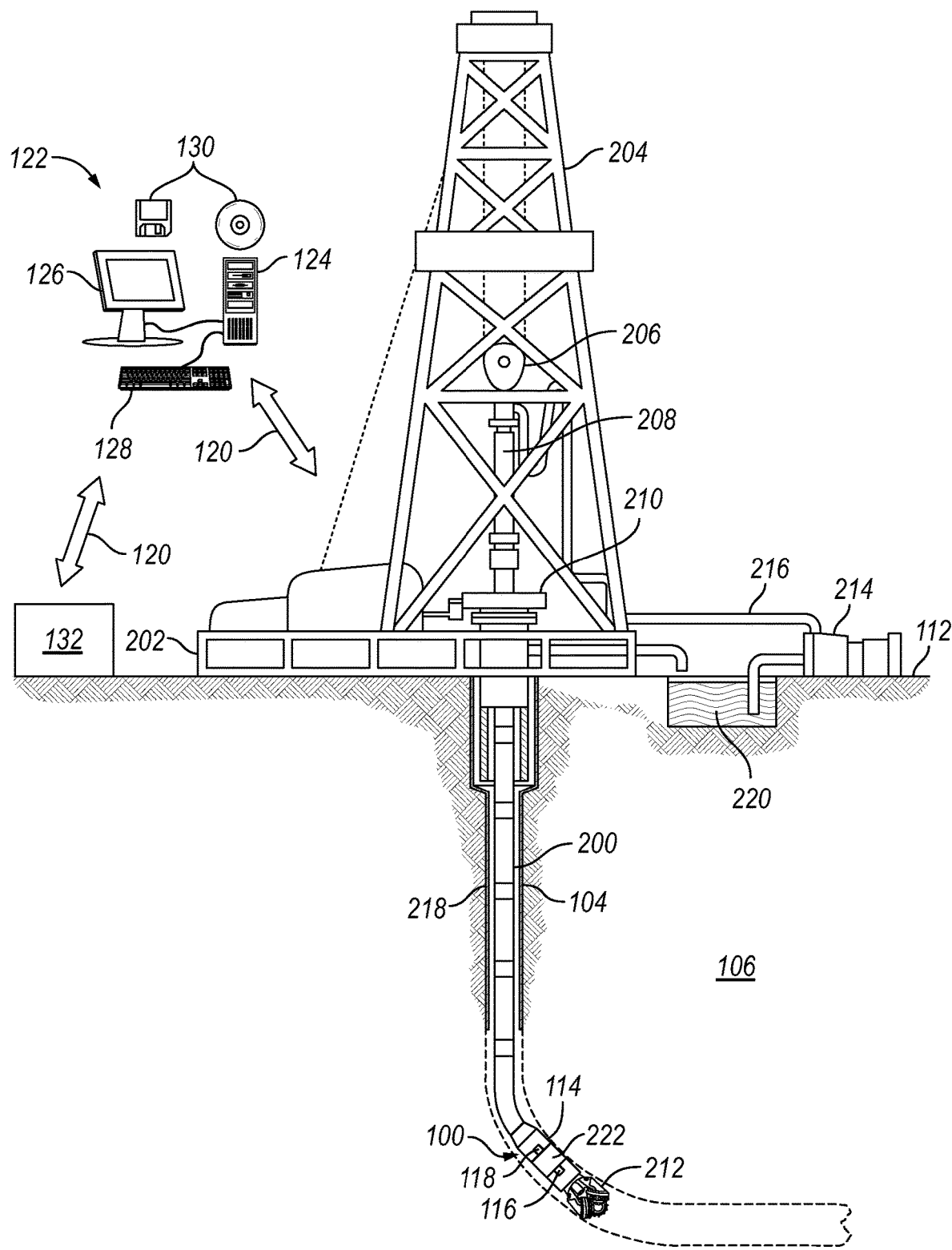
FIG. 2 is a schematic diagram of an example downhole formation rotary coring tool on a drill string.

Downhole formation rotary coring tool 100 may be used to obtain a rotary core, for example, a rotary core of a particular geology from subterranean formation 106. Rotary coring tool 100 may employ a coring bit that is deployed into the formation and drilled to a certain distance. After which, the core is broken from the formation and retrieved into the tool. Next a push rod pushes the core and deposits it into a coring tube that holds a number of cores obtained in a similar manner from different depths within the wellbore. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 2 shows a vertical or low inclination angle well, high inclination angle or horizontal placement of the well and equipment is also possible. It should further be noted that while FIG. 2 generally depicts a land-based operation, those skilled in the art will readily recognize that the principles described herein are equally applicable to subsea operations that employ floating or sea-based platforms and rigs, without departing from the scope of the disclosure.

Referring now to FIG. 2, formation rotary coring tool 100 may be disposed within a drilling operation 200. As illustrated, a drilling platform 202 may support a derrick 204 having a traveling block 206 for raising and lowering drill string 200. Drill string 200 may include, but is not limited to, drill pipe and coiled tubing, as generally known to those skilled in the art. A kelly 208 may support drill string 200 as it may be lowered through a rotary table 210. A drill bit 212 may be attached to the distal end of drill string 200 and may be driven either by a downhole motor and/or via rotation of drill string 200 from the surface 112. Without limitation, drill bit 212 may include, roller cone bits, PDC bits, natural diamond bits, any hole openers, reamers, coring bits, and the like. As drill bit 212 rotates, it may create and extend wellbore 104 that penetrates various subterrancan formations 106. A pump 214 may circulate drilling fluid through a feed pipe 216 to kelly 208, downhole through interior of drill string 200, through orifices in drill bit 212, back to surface 112 via annulus 218 surrounding drill string 200, and into a retention pit 220.

Drill bit 212 may be just one piece of a downhole assembly that may include one or more drill collars 222 and downhole formation rotary coring tool 100. Downhole formation rotary coring tool 100, which may be built into the drill collars 222 may gather measurements and rotary cores as described herein. One or more of the drill collars 222 may form a tool body 114, which may be elongated as shown on FIG. 2. Tool body 114 may be any suitable material, including without limitation titanium, stainless steel, alloys, plastic, combinations thereof, and the like. Downhole formation rotary coring tool 100 may be similar in configuration and operation to downhole formation rotary coring tool 100 shown on FIG. 1 except that FIG. 2 shows downhole formation rotary coring tool 100 disposed on drill string 200. Alternatively, formation rotary coring tool 100 may be lowered into the wellbore after drilling operations on a wireline.

Downhole formation rotary coring tool 100 may further include one or more sensors 116 for measuring reservoir and geologic properties of core sample, wellbore 104, subterranean formation 106, and/or the like. Downhole formation rotary coring tool 100 may be used to collect a rotary core sample from subterranean formation 106. Downhole formation rotary coring tool 100 may obtain and separately store different rotary core samples from subterranean formation 106 with one or more formation analysis module 118. Formation analysis module 118 may operate and function in the same manner as described above.

As previously described, information from downhole formation rotary coring tool 100 may be transmitted to an information handling system 122, which may be located at surface 112. As illustrated, communication link 120 (which may be wired or wireless, for example) may be provided that may transmit data from downhole formation rotary coring tool 100 to an information handling system 111 at surface 112. Information handling system 140 may include a processing unit 124, a monitor 126, an input device 128 (e.g., keyboard, mouse, etc.), and/or computer media 130 (e.g., optical disks, magnetic disks) that may store code representative of the methods described herein. In addition to, or in place of processing at surface 112, processing may occur downhole (e.g., fluid analysis module 118). In examples, information handling system 122 may perform computations to derive geological and reservoir properties.

Figure 3:
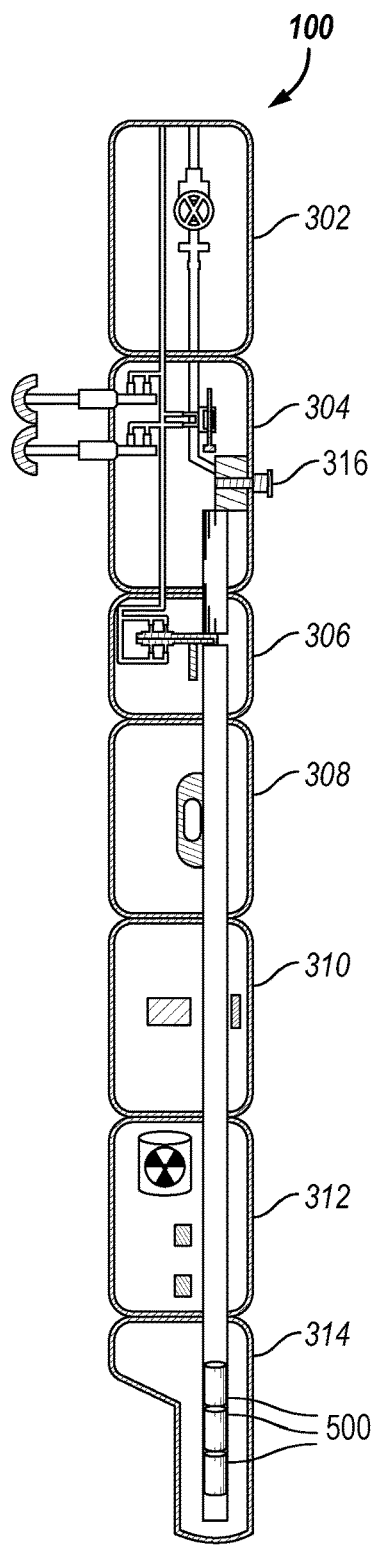
FIG. 3 illustrates a schematic view of a downhole formation rotary coring tool.

FIG. 3 illustrates a schematic view of downhole formation rotary coring tool 100. As illustrated, downhole formation rotary coring tool 100 may include one or more modules. For example, modules may comprise, but are not limited to, a motor module 302, a coring module 304, a core marker module 306, a core nuclear magnetic resonance (NMR) module 308, a core imaging analysis module 310, a core pulsed neutron analysis module 312, and/or a core storage module 314. As will be discussed in further detail below, distances between each module may be utilized for identifying one or more properties of a rotary core sample. In examples, side drill 316 may drill into formation 106 (e.g. referring to FIG. 1) and extract rotary core sample 500. Once extracted, rotary core sample 500 may move into coring module 304 and core tube 504. To be discussed in detail below, rotary core sample 500 may be transported to core marker module 306, core nuclear magnetic resonance (NMR) module 308, core imaging analysis module 310, core pulsed neutron analysis module 312, and/or a core storage module 314 via core tube 504. Herein, a module is defined as a distinct housing that provides a structural support for one or more sensor, devices, and/or the like that may measure properties of a rotary core sample. Additionally, a module may connect to other modules to form formation rotary coring tool 100. Additionally, a module may comprise a walled shell that form the outer area of each housing. Within the walled shell are the structural supports that may connect the one or more sensors, devices, and/or the like to the module. In examples, each module may have one or more individual pipes in which may allow the rotary core sample 500 may move through the module. As discussed in further detail below, each module may connect to another module and one module may be exchanged and replaced with a different module.

Figure 4:
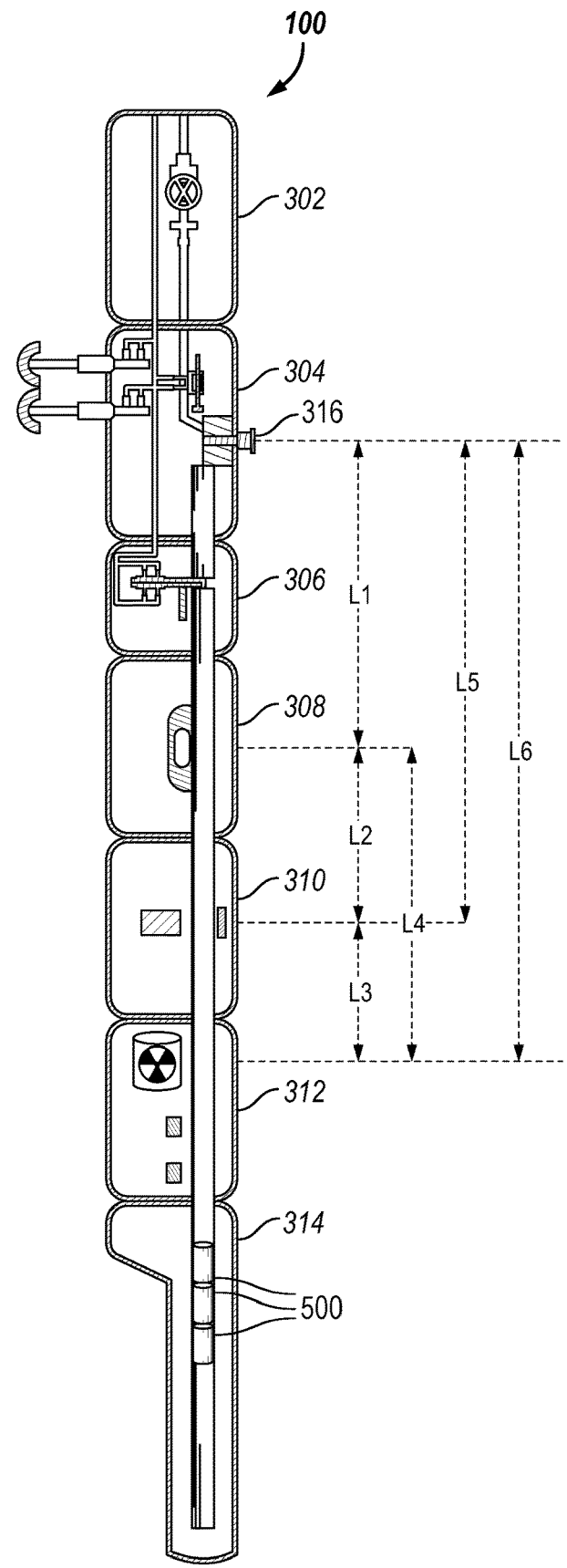
FIG. 4 illustrates different lengths between modules on a downhole formation rotary coring tool.

FIG. 4 illustrates different lengths that may be utilized during measurement operations of the rotary core sample. As illustrated, L1 may be a distance from the center of coring module 304 to the center of NMR module 308. L2 may be a distance from the center of core NMR module 308 to the center of core imaging analyses module 310. L3 may be a distance from the center of core imaging analyses module 310 to the center of core pulsed neutron analysis module 312. L4 is a distance from the center of core NMR module 308 to the center of core pulsed neutron analysis module 312. L5 may be a distance from the center of core module 304 to the center of core imaging analyses module 310. L6 is a distance from the center of core module 304 to the center of core pulsed neutron analysis module 312.

Figure 5:
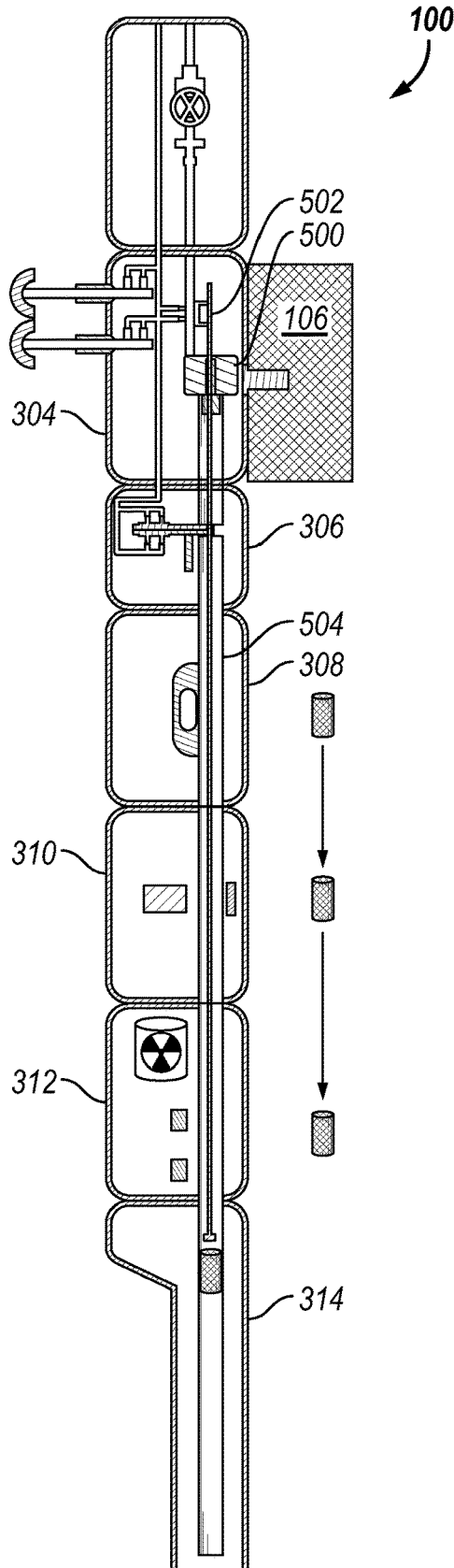
FIG. 5 illustrates one or more examples of measuring a rotary core sample during measurement operations.

FIG. 5 illustrates one or more examples of measuring a rotary core sample 500 during measurement operations. As illustrated, within downhole formation rotary coring tool 100, coring module 304 may remove a rotary core sample 500 from subterranean formation 106 into an individual tube. The individual tube may form a segment of core tube 504. Disposed within coring module 304, push rod 502 may be configured to transport rotary core sample 500 at any selected speed through the channel formed from the core tube 504. Push rod 502 may be controlled by and connected to one or more devices within a motor module 302. Push rod 502 is controlled electro-mechanically. Motor module 302 may include a hydraulic line connected to the push rod 502 through relays. The relays that control the function "Rod Extend" and "Rod Retract". Multiple push rods 502 may be comprised for each relay. When the Operator toggles either relay, it may be actuated and hydraulic pressure increases pushing push rod 502 down or depletes, retracting the rod to its original position.

Additionally, core tube 504 may traverse through coring module 304, core marker module 306, core NMR module 308, core imaging analysis module 310, core pulsed neutron analysis module 312, core storage module 314, and/or any module that may comprise downhole formation rotary coring tool 100. Obtaining rotary core sample 500 may be performed in a wireline or drilling implementation. Core storage module 314 comprises an individual tube which may store core samples 500. Core samples 500 may be stored within core storage module until formation rotary coring tool 100 is returned to the surface.

Figure 6A:
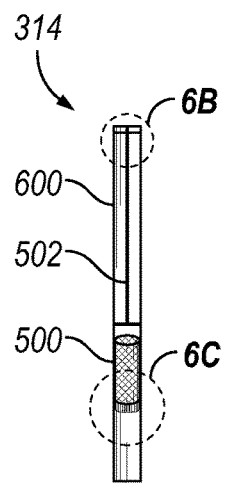
FIGS. 6A, 6B, and 6C illustrate a core tube and associated components.
Figure 6B:
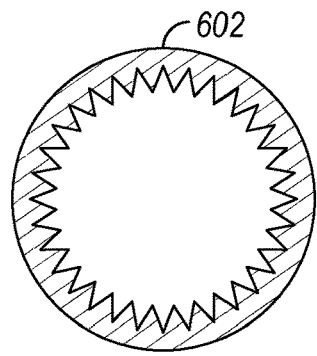
Figure 6C:
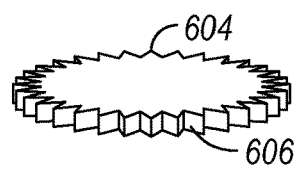

FIG. 6 illustrates core tube 504. Core tube 504 may comprise a core tube wall 600 in which push rod 502 moves rotary core sample 500 through. Core tube 504 may extend the length of downhole sampling tool 100 (i.e. from core module 304 to core storage module 314). To control the speed of rotary core sample 500 as it travels along core tube 504, the inner surface of core tube wall 600 may be lined with rigid edges 602. Rigid edges 602 may take any acceptable shape. Ridged edges 602 may be designed to provide adequate friction based on the wellbore environment and rock sample being run. Wellbore environment details include wellbore fluid type (water based mud, oil based mud, air, diesel, brine), pressure and temperature. The shape of the rigid edges 602 may be triangular, square, or tapered off in either a triangular, square or circular form. Additionally, a friction guide marker 604 may be disposed below rotary core sample 500. Friction guide marker 604 may hold rotary core sample 500 in place while it traverses through formation rotary coring tool 100. It also serves as a separation marker in the tube from other cores, so when they are retrieved, they can be designated individually Friction guide marker 604 may include rigid surface 606 that may fit within rigid edges 602 of core tube wall 600. Rigid surface 606 may comprise friction along rigid edges 602, which may prevent rotary core sample 500 from moving freely within core tube 504. A special coating may be layered on top to aid in travel for a certain speed beside module. As rotary core sample 500 is transported through core tube 504 by motor modules 302 with push rod 502 to core storage module 314, one or more modules may analyze rotary core sample 500.

FIG. 7 illustrates core NMR module 308. Core NMR module 308 may comprise a module housing 700, a magnet 702, an antenna 704, and an individual tube which forms a segment of core tube 504. During measurement operations utilizing core NMR module 308, magnet 702 may polarize Hydrogen nuclei within rotary core sample 500. Subsequently, antenna 704 may emit a transmit pulse 706 into rotary core sample 500 to excite Hydrogen nuclei within rotary core sample 500. Antenna 704 may then sense, measure, and/or record receive pulse 706 that is reflected from rotary core sample 500. Specifically, antenna 704 may sense, measure, and/or record T1 and T2 relaxation times of Hydrogen nuclei that are within rotary core sample 500.

FIGS. 8A and 8B illustrate that the amount of time taken to relax is an indication of pore size and fluid inside the pore. In particular, FIG. 8A illustrates the amplitude over time of the response from antenna 704. FIG. 8B is generated by "stacking" multiple received echoes (e.g. referring to FIG. 8A) over a time period and generating a graph representative of porosity of the formation. From this, a time inversion is made to show an estimate of permeability and the type of fluid. From this measurement, an estimate of porosity, porosity, fluid typing, and fluid mobility may be obtained.

Figure 9A:
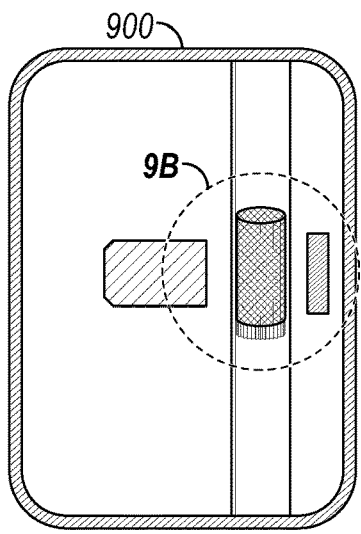
FIGS. 9A and 9B illustrate the side and top profiles, respectively, of a core imaging analysis module.
Figure 9B:
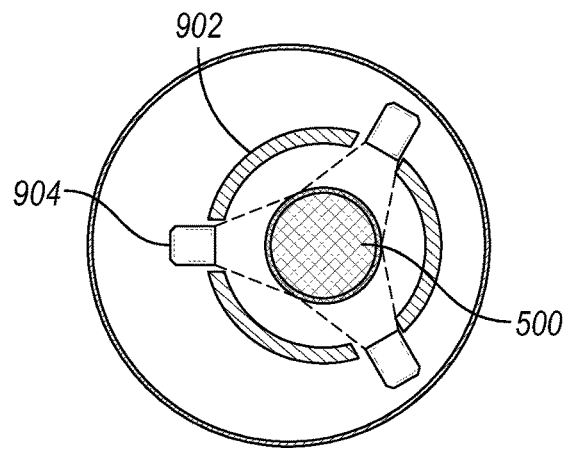

FIG. 9A illustrates core imaging analysis module 310. As illustrated, core imaging analysis module 310 may comprise module housing 900 in which one or more imaging sources may be disposed and an individual tube which forms a segment of core tube 504. For example, imaging sources may comprise any combination of, but are not limited to, microresistivity, computed tomography, or ultrasound technologies. FIG. 9B illustrates a top view of core imaging analysis module 310. In examples, rotary core sample 500 may be imaged by an x-ray detector 902 which may include on or more x-ray sources 904. In this example, rotary core sample 500 may be imaged to provide 360 degrees of circumferential coverage.

Figure 10:
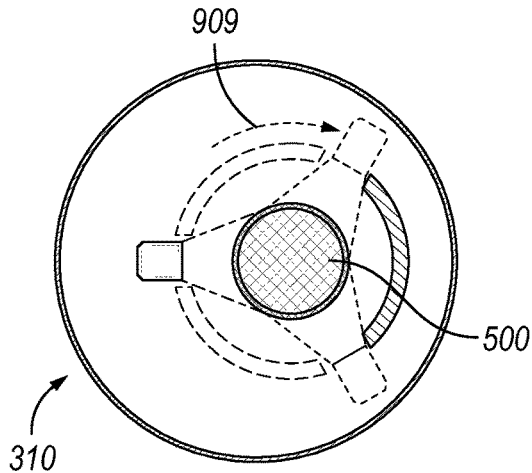
FIG. 10 illustrates a core imaging analysis module.

FIG. 10 illustrates core imaging analysis module 310 in which a single X-ray source 904 rotates around rotary core sample 500. As a result, imaging analysis module may provide 360 degrees of circumferential coverage from an X-ray source.

Figure 11A:
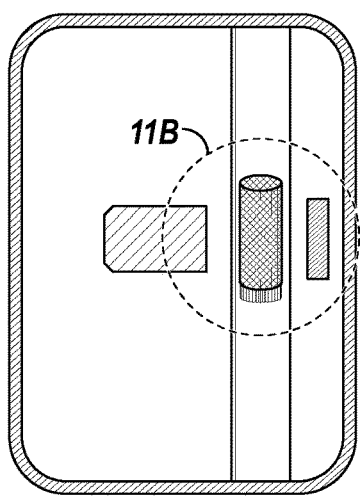
FIGS. 11A and 11B illustrate the side and top profiles, respectively, of a core imaging analysis module.
Figure 11B:
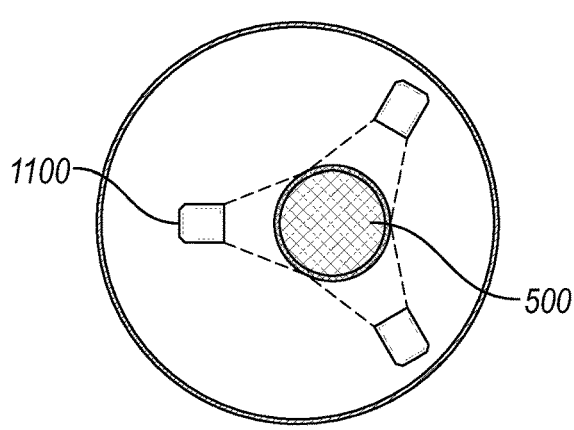

FIGS. 11A and 11B illustrate core imaging analysis module 310 in which one or more ultrasonic devices 1100 are present and an individual tube which forms a segment of core tube 504. In examples, ultrasonic devices 1100 may operate and function as both transmitters and receivers. Additionally, ultrasonic devices 1100 may provide 360 degrees of circumferential coverage for rotary core sample 500. FIG. 12 illustrates core imaging analysis module 310 in which a single ultrasonic device 1100 rotates around rotary core sample 500 to provide 360 degrees of circumferential coverage.

FIGS. 13A-13C illustrate core imaging analysis module 310 in microstrip device 1300 may be utilized to provide circumferential coverage of rotary core sample 500 and an individual tube which forms a segment of core tube 504. Microstrip device 1300 may operate and function as both a transmitter and receiver. Microstrip device 1300 provide 360 degrees of circumferential coverage. As illustrated in FIG. 13C microstrip device 1300 may comprise one or more sensors and/or resonators 1302. Sensors and/or resonators 1302 may measure formation permittivity and resistivity of rotary core sample 500 that in turn can be processed to resolve an image of the core. Such measurements may be used to resolve additional characteristics that ultrasound and CT cannot provide.

Figure 14B:
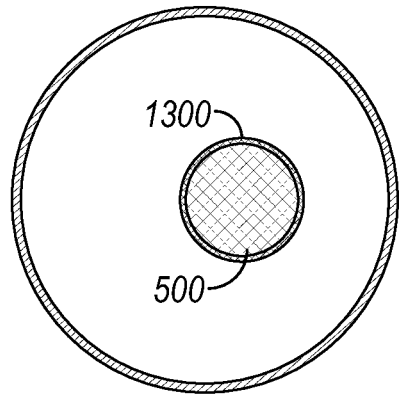
FIGS. 14A-14C illustrates another example of the core imaging analysis module.
Figure 14A:
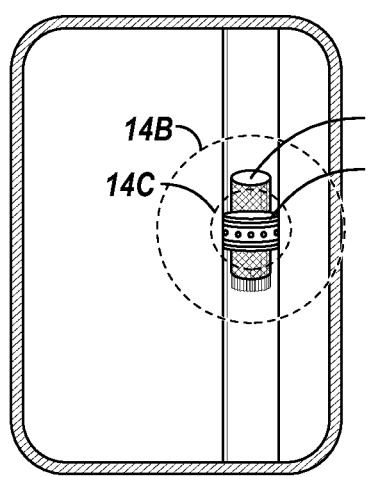
Figure 14C:
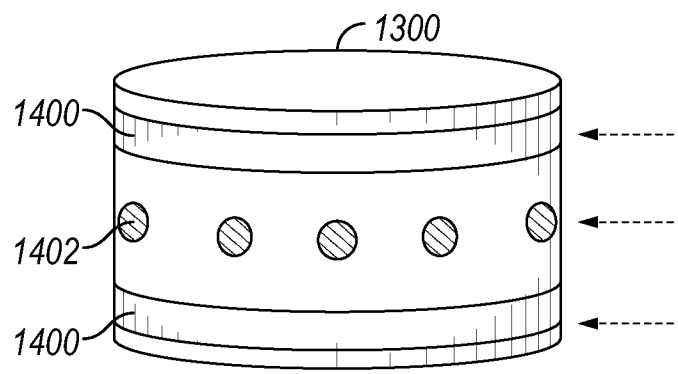

FIGS. 14A-14C illustrate core imaging analysis module 310 in microstrip device 1300 may be utilized to provide circumferential coverage of rotary core sample 500, which may operate and function as both transmitters and receivers, provide 360 degrees of circumferential coverage. Additionally, FIG. 14A shows an individual tube which forms a segment of core tube 504. As illustrated in FIG. 13C microstrip device 1300. As illustrated, microstrip device 1300 may be an electrode-based technology. Thus, microstrip device 1300 may comprise one or more return electrodes 1400 and one or more emitters 1402.

Figure 15A:
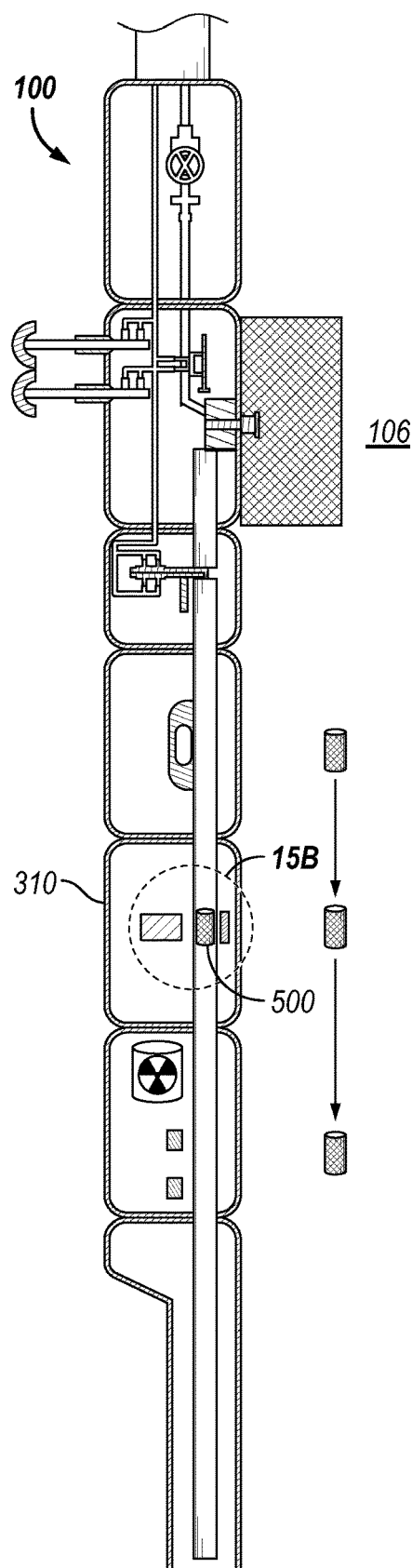
FIGS. 15A-15D illustrate downhole formation rotary coring tool during measurement operations.
Figure 15B:
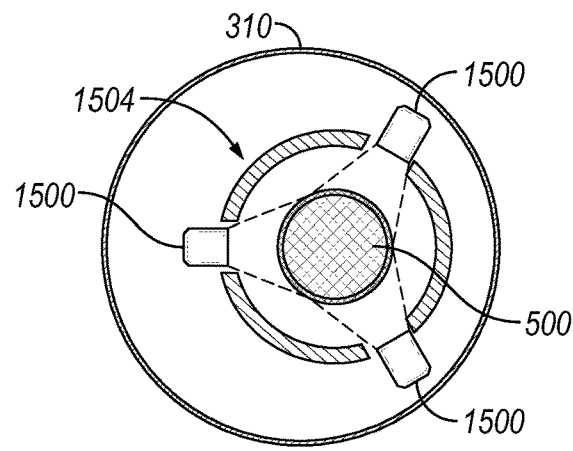

FIGS. 15A and 15B illustrate downhole formation rotary coring tool 100 during measurement operations. During measurement operations, downhole formation rotary coring tool 100 may remove a rotary core sample 500 from formation 106, as previously described. As illustrated in FIG. 15B, rotary core sample 500 may be marked with earth coordinates of where rotary core sample 500 was taken, with the use of an inclinometry tool in combination. Herein, earth coordinates may be defined as the measured depth, direction, and/or azimuth of the core. With earth coordinates, the top side of rotary core sample 500 may be determined. Then as rotary core sample 500 passes through the imaging module, all the measured features of the rock can be designated relative to the Earth Coordinates.

Figure 15C:
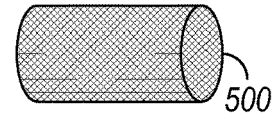
Figure 15D:
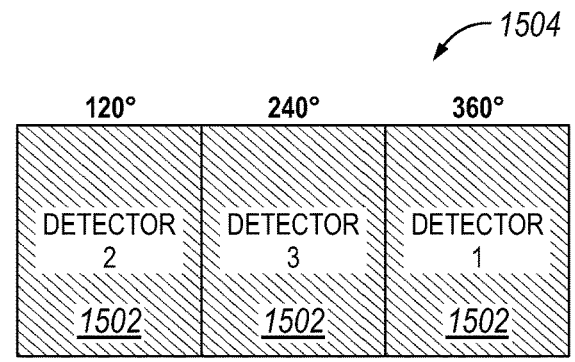

Additionally shown, core imaging analysis module 310 may analyze rotary core sample 500 from FIG. 15C in 360 degrees, using methods and systems as discussed above, illustrated in FIG. 15D. One or more detectors 1500 may utilize imaging sources to obtain images. As illustrated in FIG. 15D, images formed may be complete images 1504 or individual images 1502 stacked into a complete image via a 360 degree implementation of detectors 1500, as illustrated. Image types may be any combination of, but are not limited to, microresistivity, computed tomography, or ultrasonic technologies of. Detectors 1500 may comprise any combination of X-ray sources, ultrasonic devices, microstrip devices, and the like.

Figure 16A:
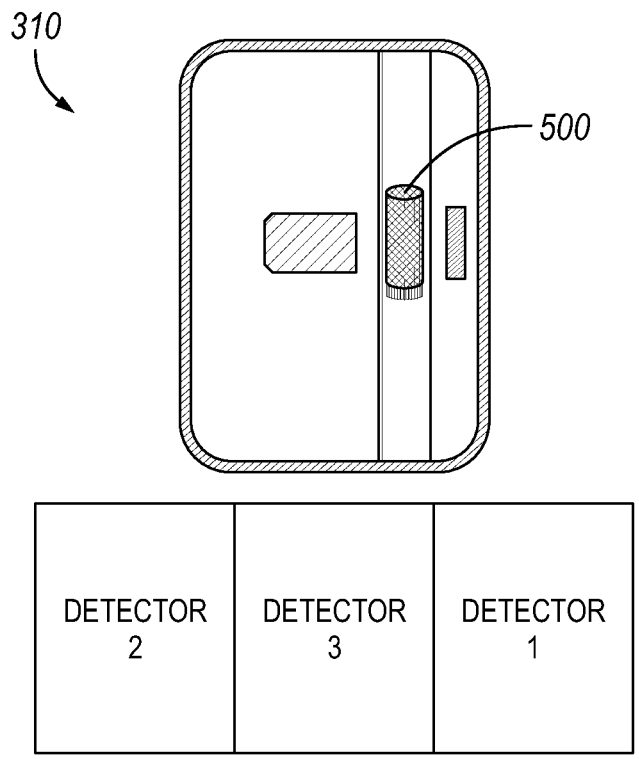
FIGS. 16A-16D illustrate another method utilizing core imaging analysis module.
Figure 16B:
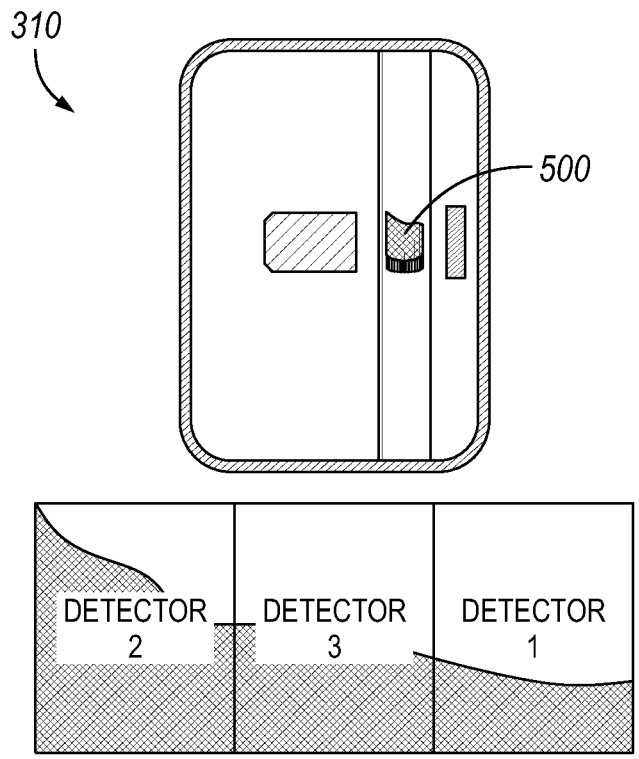
Figure 16C:
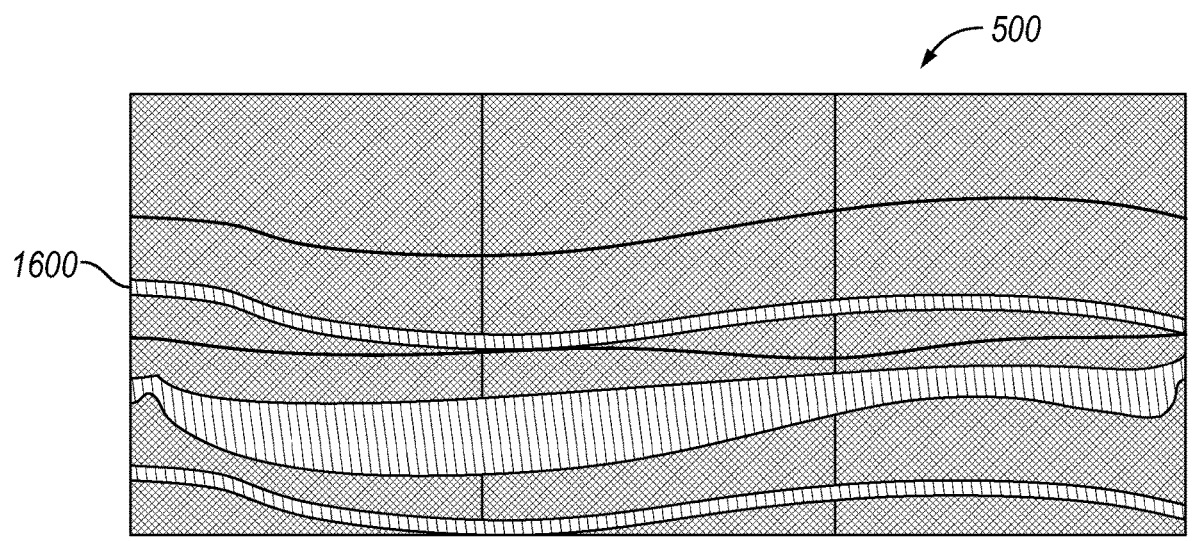
Figure 16D:
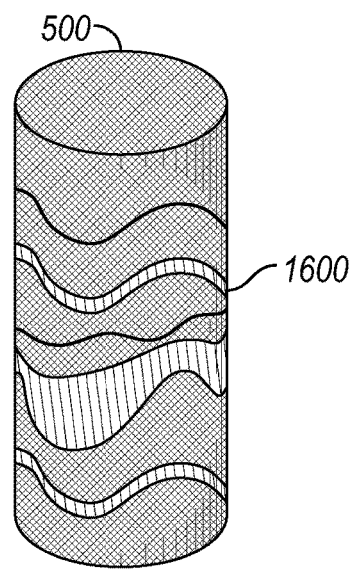

FIGS. 16A-16D illustrate another method utilizing core imaging analysis module 310. In this operation the integrity of rotary core sample 500 is identified while downhole. Herein, integrity of rotary core sample 500 is a core captured in full length and diameter intended with the core bit. Should rotary core sample 500 show fractured or an incomplete length, rotary core sample 500 may be recaptured. This may allow operators to determine if another rotary core sample 500 may be needed in a similar zone or if downhole formation rotary coring tool 100 may move to another area. As illustrated, downhole formation rotary coring tool 100 may perform an analysis on rotary core sample 500 while intact. Currently, a number of rotary core sample 500 may arrive at the surface dismantled, preventing a core analysis from being performed. However, FIG. 16B illustrates processing on a partial section for rotary core sample 500. FIG. 16C identifies a two-dimensional image rotary core sample 500 was extracted from. As illustrated in FIGS. 16D and 16E, downhole formation rotary coring tool 100 may allow one to obtain rock laminations, bedding planes and stratigraphy of rotary core sample 500 through imaging analyses described above. This may allow for a correlation between one or more geologic zone in real time.

FIG. 17A illustrates a core pulsed neutron analysis module 312 and an individual tube which forms a segment of core tube 504. As illustrated, core pulsed neutron module 312 may comprise of a pulsed neutron generator disposed in module 1702 that emits a burst of high energy neutrons that interact with rotary core sample 500 disposed in core tube 504. This interaction results in inelastic gamma rays 1704 and captured gamma rays 1706, which may be detected by detector 1708. FIG. 17B is a graph of measurements for an inelastic spectra and FIG. 17C is a graph of measurements for a capture spectra. Within each burst, timing gates are used to compute relative concentrations of elements that exist in the rock, known as Elemental Yields. Using the Elemental Yields computation, the following element concentrations may be obtained but not limited to: Aluminum Al, Barium Ba, Carbon C, Calcium Ca, Chlorine Cl, Iron Fe, Gadolinium Gd, Potassium K, Magnesium Mg, Manganese Mn, Sodium Na, Sulfur S, Silicon Si, and/or Titanium Ti. These elements may be correlated to different minerals in the rock that may include: Quartz, Feldspars, Micas, Calcite, Dolomite, Clay, Iron, and/or Evaporites and be used to derive various answer products such as Total Organic Carbon (TOC). In addition, downhole formation rotary coring tool 100 may operate in a sigma or Carbon Oxygen mode to derive saturations of oil, water, and/or gas.

Figure 18A:
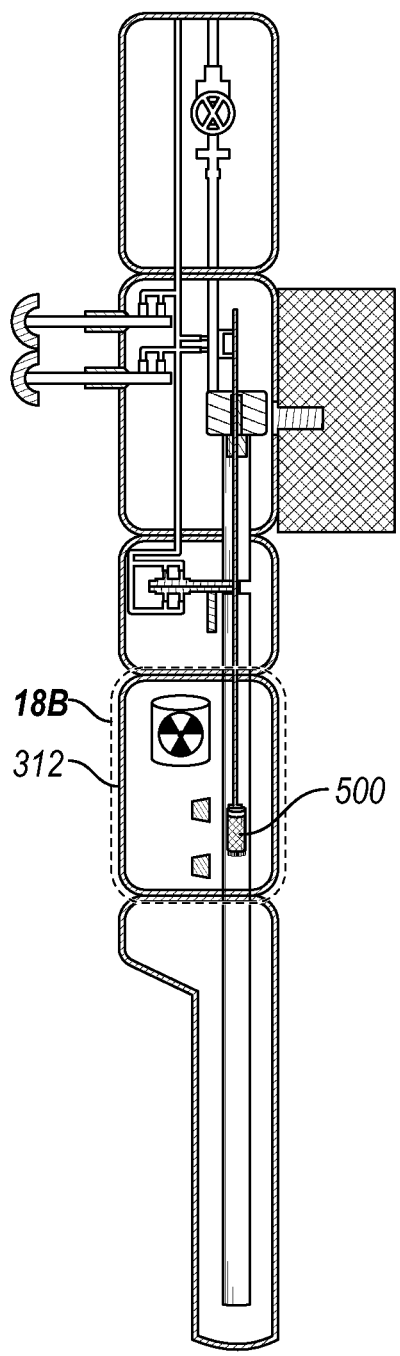
FIGS. 18A-C illustrate neutron analysis module.
Figure 18B:
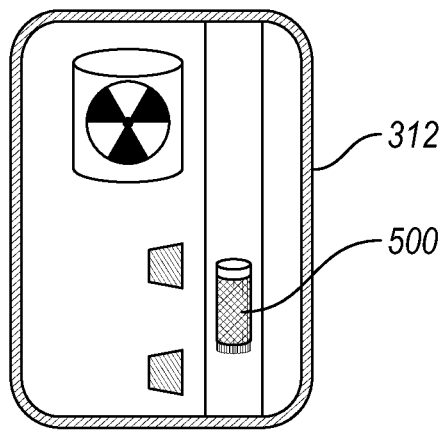
Figure 18C:
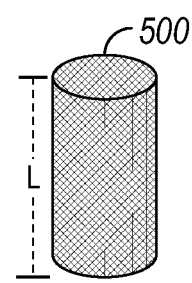
Figure 19A:
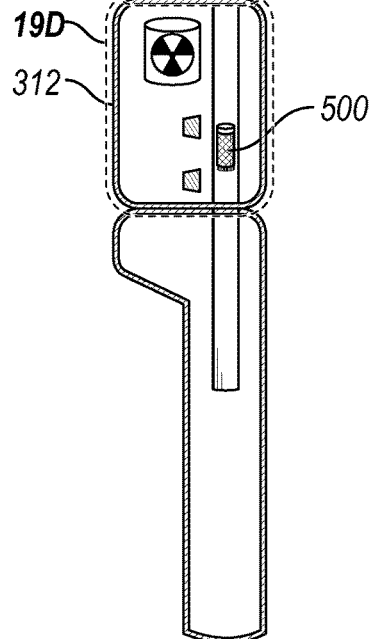
FIG. 19A-E illustrate an example for identifying volume of a gas in rotary core sample with core imaging analysis module.
Figure 19B:
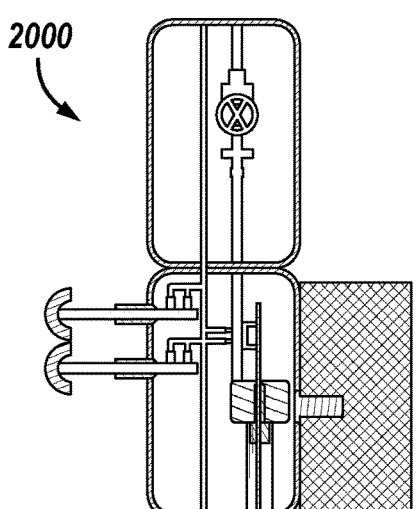
Figure 19C:
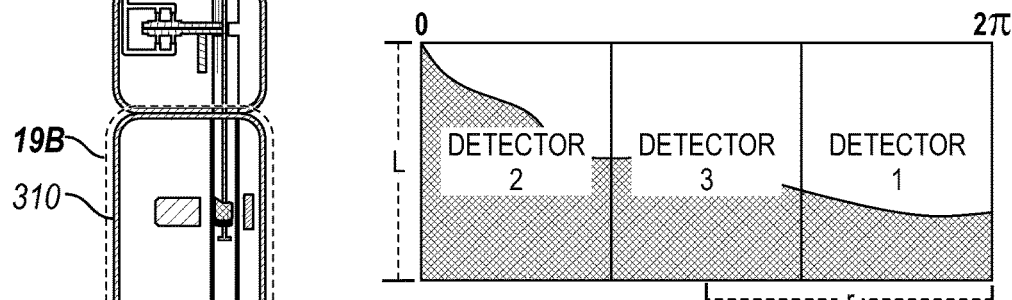
Figure 19D:
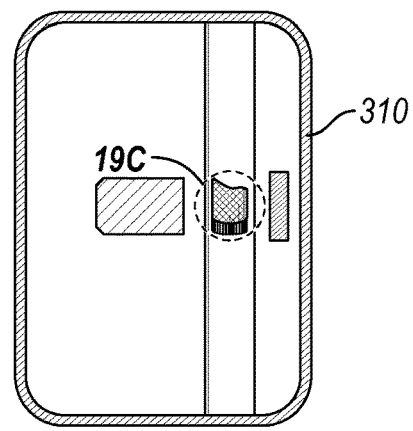
Figure 19E:
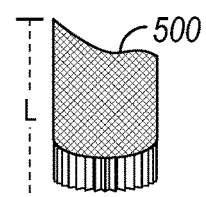

FIGS. 18A-C illustrate another example of neutron analysis module 312 and core imaging analysis module 310 and an individual tube which forms a segment of core tube 504. Neutron analysis module 312 may further be implemented for obtaining a volume of a gas in rotary core sample 500. As illustrated, downhole formation rotary coring tool 100 may utilize core pulsed neutron analysis module 312 for identifying the volume of gas in rotary core sample 500. To do this, the radius and length of rotary core sample 500 is found using push rod 502 which measures length of the core by measuring the core against a plate (not illustrated) in the marker module 306. Then the plate opens and it is deposited into the tube.

Using such measurements, gas saturation may be derived through a ratio of inelastic to slow capture counts, which may be obtained in core pulsed neutron analysis module 312. This ratio of counts captured vs counts emitted by the radiation source can be calculated to provide saturations of gas, oil or water. With these measurements and information, volume of a gas may be calculated using:

$$V_{core} = \pi r^2 L \quad (1)$$

where $$V_{gas} = (V_{core})(Saturation_{Gas}) \quad (2)$$

Therefore, utilizing equations (1) and (2) with measurements from marker module 306 and neutron analysis module 312, we may obtain $V_{gas}$.

FIG. 19A-E illustrate an example for identifying volume of a gas in rotary core sample 500 with core imaging analysis module 310 and an individual tube which forms a segment of core tube 504. In this example imaging analysis may be utilized in conjunction with core pulsed neutron analysis module 312. As illustrated, core imaging analysis module 310 may produce an image 1900 of rotary core sample 500 using the methods and systems described above. Using these measurements, gas saturation may be derived through a ratio of inelastic to slow capture counts, which may be obtained in core pulsed neutron analysis module 312. Gas volume is Saturation of Gas times total volume of the core. The module measures saturation, and a calculation would be performed to derive $V_{gas}$. Core imaging analysis module 310 may calculate $V_{core}$. The integrity of the core and calculating the length, and then the radius, a total volume can be calculated. This value is then fed into the calculation for $V_{gas}$. With these measurements and information, volume of a gas may be calculated using:

$$V_{core} = \int_0^L dz \int_0^{2\pi} d\theta \int_0^r dr \quad (3)$$

where $$V_{gas} = (V_{Core})(Saturation_{Gas}) \quad (4)$$

Therefore, utilizing equations (3) and (4) with measurements from marker module 306 and neutron analysis module 312, we may obtain $V_{gas}$.

Figure 20D:
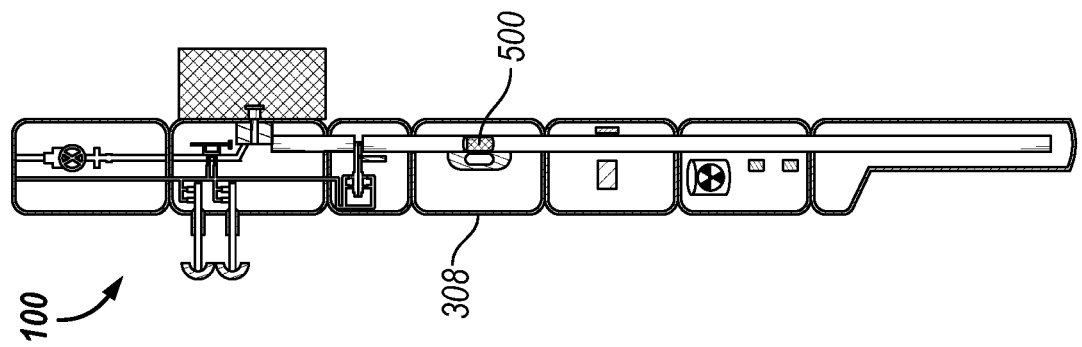
FIG. 20A-20G illustrate one or more measurements being performed on rotary core sample during measurement operations by downhole formation rotary coring tool.
Figure 20C:
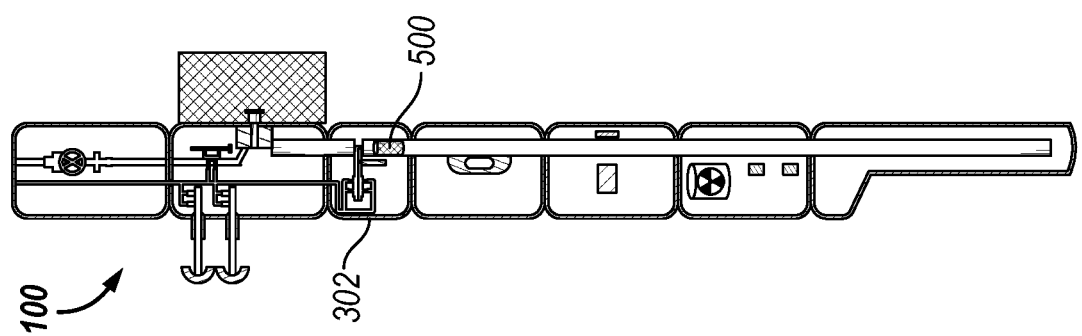
Figure 20B:
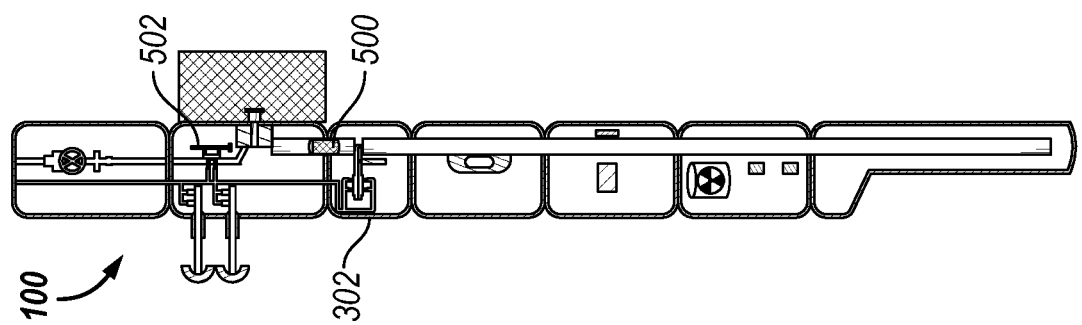
Figure 20A:
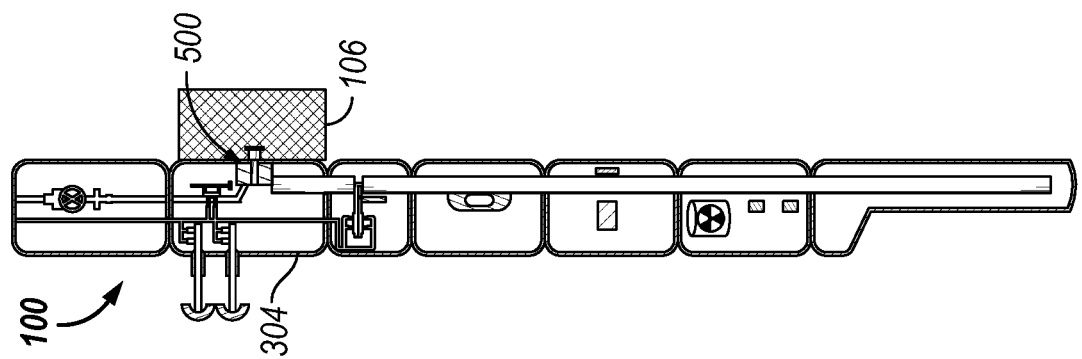

FIGS. 20A-20G illustrate one or more measurements being performed on rotary core sample 500 during measurement operations by downhole formation rotary coring tool 100. FIG. 20A illustrates the removal of rotary core sample 500 from subterranean formation 106 with core module 304. In FIG. 20B, the length of rotary core sample 500 is measured with a push rod 502 in core marker module 306. Push rod 502 controls the rate rotary core sample 500 is cored and moves through downhole coring tool 100. Additionally, core marker module 306, further illustrated in FIG. 20C, marks rotary core sample 500, and a friction guide marker 604 (e.g. referring to FIG. 6) is disposed below rotary core sample 500.

Figure 20E:
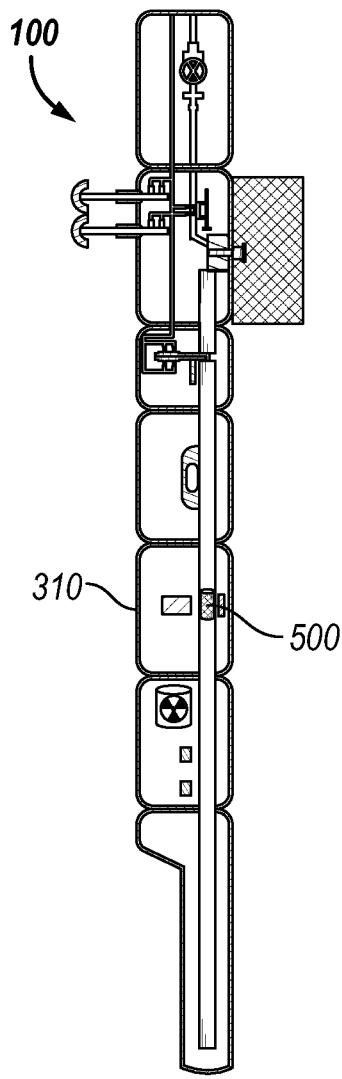
Figure 20F:
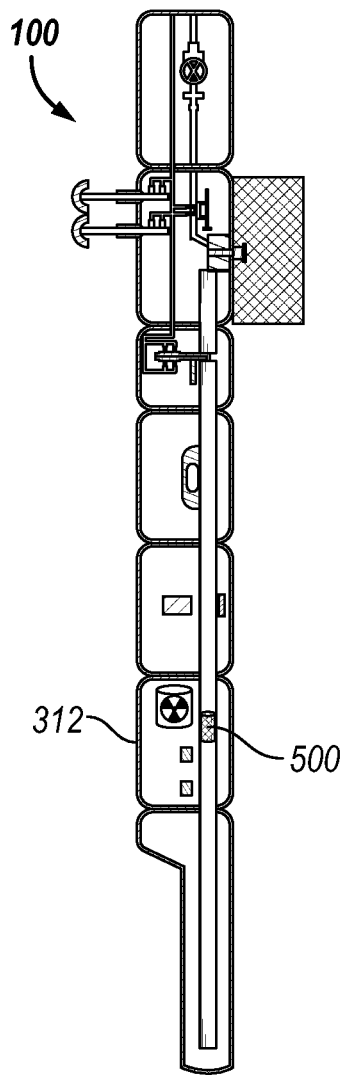
Figure 20G:
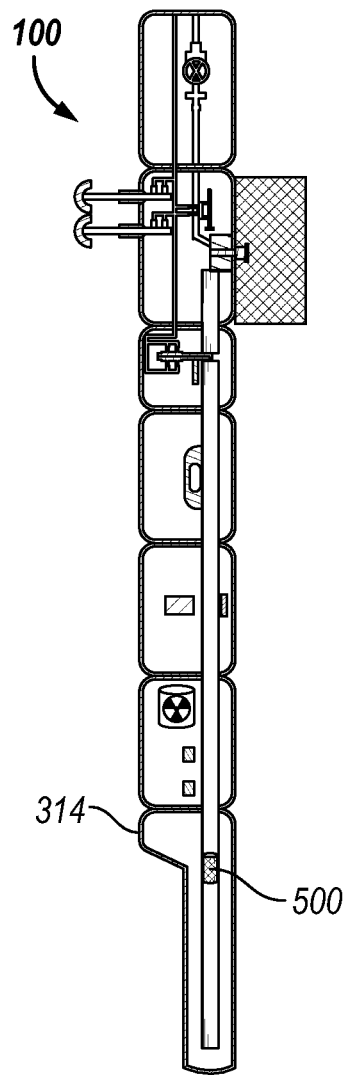

FIGS. 20D-20F illustrate measurement operations that may be performed on rotary core sample 500. For example, FIG. 20D illustrates rotary core sample 500 being measured by core NMR module 308, as previously described. FIG. 20E illustrates rotary core sample 500 being measured by core imaging analysis module 310, as previously described. FIG. 20F illustrates rotary core sample 500 being measured by core pulsed neutron analysis module 312. After measurements have been performed, as described above, rotary core sample 500 may be deposited into core storage module 314, as illustrated in FIG. 20G, which may allow for personnel to remove one or more rotary core samples 500 after downhole operations have been completed. Once a rotary core sample 500 is stored, push rod 502 may return to coring module 304 for another sample. Any number of samples may flow through downhole sampling tool 100 at a consistent or inconsistent rate.

Figure 21:
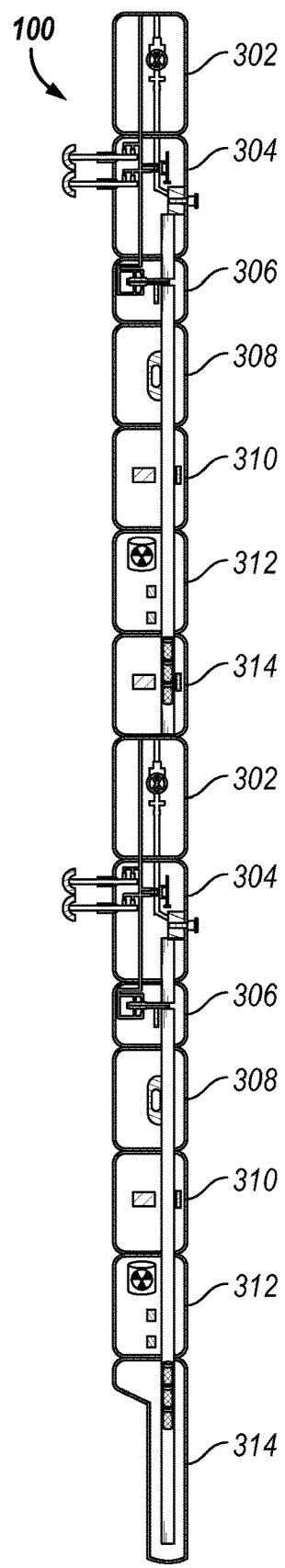
FIG. 21 illustrates another example of the downhole formation rotary coring tool.

FIG. 21 illustrates another an example of downhole formation rotary coring tool 100 which may include a plurality of motor modules 302, a plurality of coring modules 304, a plurality of core marker modules 306, a plurality of core NMR modules 308, a plurality of a core imaging analysis modules 310, a plurality of core pulsed neutron analysis modules 312, and/or a core storage modules 314. As illustrated, motor module 302, coring module 304, core marker modules 306, core NMR modules 308, core imaging analysis modules 310, core pulsed neutron analysis modules 312, and/or core storage modules 314 each comprise individual tubes. Each individual tube allows for transportation of rotary core sample 500 (e.g. referring to FIG. 5) through their respective module. Any number of modules connected together, forms core tube 504.

Figure 22:
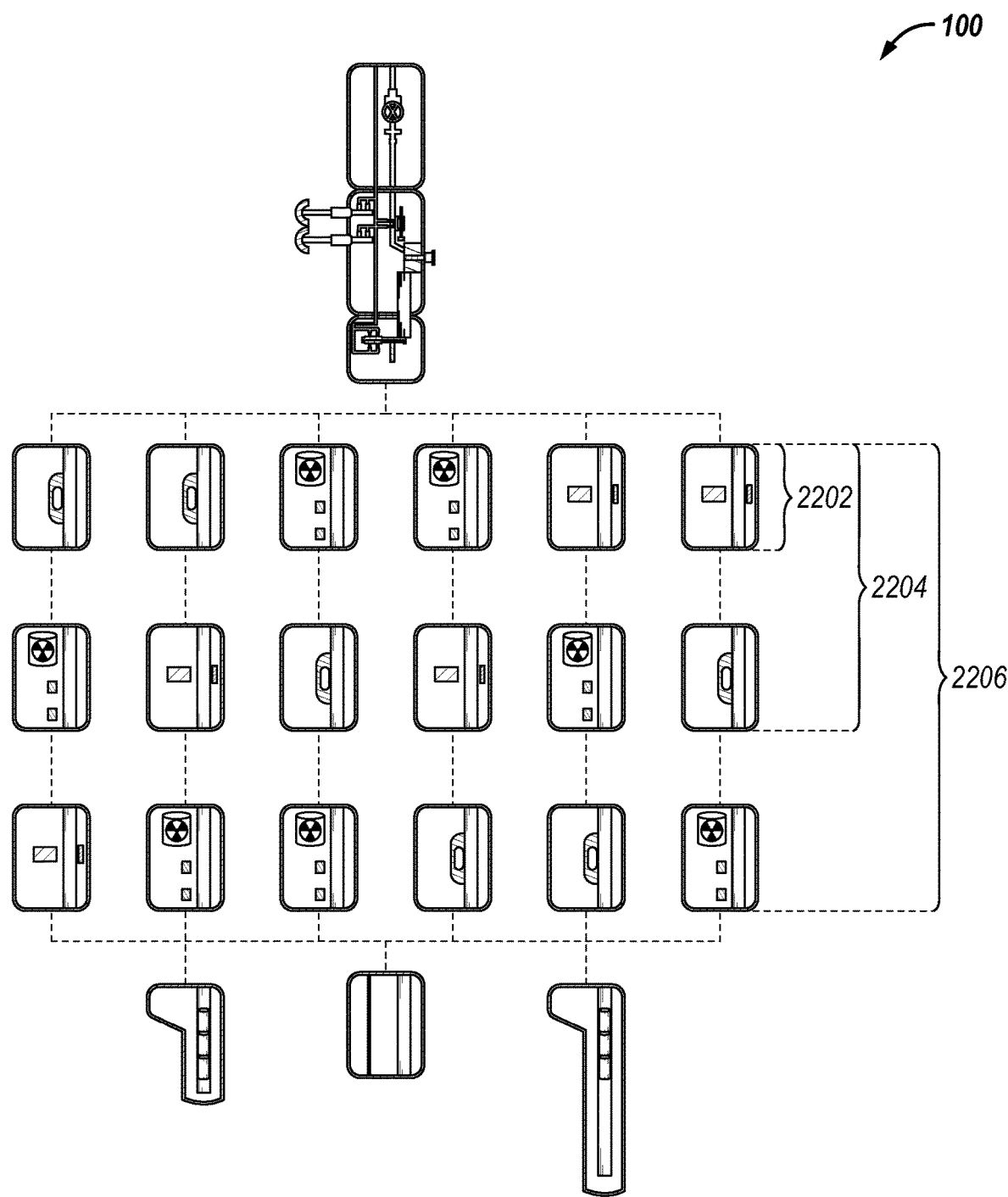
FIG. 22 one or more arrangements of sensing modules in the downhole formation rotary coring tool.

FIG. 22 illustrates that downhole formation rotary coring tool 100. As previously illustrated, formation rotary coring tool 100 has been provided in the preceding order of NMR module 308, core imaging analysis modules 310, and finally core pulsed neutron analysis modules 312. However, this is only an example as any number of sensing modules in any order may be present, wherein a sensing module is an NMR module 308, a core imaging analysis modules 310, or a core pulsed neutron analysis modules 312. Additionally, as discussed above, a sensing module is defined as a distinct housing that provides a structural support for one or more sensor, devices, and/or the like that may measure properties of a rotary core sample. The support a module may comprise a walled shell that form the outer area of each housing. Within the walled shell are the structural supports that may connect the one or more sensors, devices, and/or the like to the module. Additionally, a sensing module may connect to other modules to form formation rotary coring tool 100, including but not limited to other sensing modules. Further, each sensing module may comprise individual pipes for transporting rotary core sample 500. In a first example of downhole formation rotary coring tool 100, a single module implementation 2202 may use any number of, but only a single type module from the list of an NMR module 308, a core imaging analysis modules 310, or a core pulsed neutron analysis modules 312 may be selected. Additionally, downhole formation rotary coring tool 100 may use a double module implementation 2204. Double module implementation 2204 may use any number of, but only two types of modules from the list of an NMR module 308, a core imaging analysis module 310, or a core pulsed neutron analysis module 312. The order of modules may be selected in any possible iteration. Further, downhole formation rotary coring tool 100 may use a triple module implementation 2206. Triple module implementation 2204 may use any number of an NMR module 308, a core imaging analysis module 310, or a core pulsed neutron analysis module 312. The order of modules may be selected in any possible iteration.

Measurements of core sample 500 (e.g. referring to FIG. 5) from NMR module 308, a core imaging analysis modules 310, or a core pulsed neutron analysis modules 312 may convey permeability, clay bound water, fluid typing and pores size distribution of the Core. PNL provides Elemental yields, Total Organic Carbon, and saturations of fluids in the rock. The imaging technologies provide geological features-bedding planes, stratigraphy, structure of the rock. Knowing the coordinates gives us a unique identifier of each rock that can then be correlated and integrated to a wireline interpretation of the reservoir (with other wireline sensors).

Additionally, core sample 500 may be transferred to a laboratory on the surface where similar measurements may be performed and integrated with measurements/observations downhole. Laboratories have CT and NMR technologies. And they physically measure the length and radius of the core. Pulsed Neutron has been speculated to add as a new analysis. However, they do not measure earth coordinates of the cores.

Methods and systems disclosed above are an improvement over current technology. Specifically, downhole core analysis may be performed at their respective pressure and temperature. Whereas, currently the industry performs these measurements at the surface at room temperature and pressure. Performing measurements at room temperature and pressure has an adverse effects to the integrity of the sample, and the results will be compromised.

The systems and methods disclosed herein may comprise any of the various features of the systems and methods disclosed herein, including one or more of the following statements.

Statement 1: A downhole tool comprising: a coring module for obtaining at least one rotary core sample from a formation; and a core marker module for marking the at least one rotary core sample with earth coordinates, wherein the coring module is separate from the core marker module.

Statement 2: The downhole tool of statement 1, further comprising a friction guide marker for holding the at least one rotary core sample in place within the downhole tool.

Statement 3: The downhole tool of statement 2, wherein the friction guide marker comprises a rigid surface.

Statement 4: The downhole tool of statement 3, wherein the rigid surface fits within rigid edges of a core tube of the downhole tool.

Statement 5: The downhole tool of any of statements 1-4, further comprising a core nuclear magnetic resonance module for polarizing Hydrogen nuclei within the rotary core sample.

Statement 6: The downhole tool of any of statements 1-5, further comprising a core imaging analysis module for imaging the at least one rotary core sample.

Statement 7: The downhole tool of any of statements 1-6, further comprising a core pulsed neutron analysis module for measuring the at least one rotary core sample.

Statement 8: The downhole tool of any of statements 1-7, further comprising a side drill for drilling into the formation to extract the at least one rotary core sample.

Statement 9: The downhole tool of any of statements 1-8, further comprising a core storage module for storing the at least one rotary core sample after marking the at least one rotary core sample with the core marker module.

Statement 10: The downhole tool of any of statements 1-9, further comprising a motor module that includes a hydraulic line connected to a push rod configured to toggle between retracted and extended positions to move the at least one rotary core sample along a core tube.

Statement 11: The downhole tool of any of statements 1-10, further comprising one or more sensing modules disposed within the downhole tool, wherein the second sensing module comprises an individual tube that forms part of the core tube that connects at least the coring module and the core marker module.

Statement 12: The downhole tool of statement 11, wherein the one or more sensing modules comprise at least one modules selected from the group consisting of a Nuclear Magnetic Resonance module, a core imaging analysis module, and a core pulsed neutron analysis module.

Statement 13: A method comprising: obtaining at least one rotary core sample from a formation with a coring module within a downhole tool; and marking the at least one rotary core sample with earth coordinates with a core marker module disposed within the same downhole tool, wherein the core marker module is separate from the coring module.

Statement 14: The method of statement 13, further comprising holding the rotary core sample in place within the downhole tool with a friction guide marker.

Statement 15: The method of statement 14, wherein the friction guide marker comprises a rigid surface.

Statement 16: The method of statement 14, wherein the rigid surface fits within rigid edges of a core tube of the downhole tool.

Statement 17: The method of statement 16, wherein a friction coefficient of the rigid edges and/or the rigid surface is based on at least one wellbore environment detail.

Statement 18: The method of any of statements 13-17, further comprising sensing the at least one rotary core sample with one or more sensing modules disposed within the same downhole tool, wherein the one or more sensing modules are selected from the group consisting of an NMR module, a core imaging analysis module, a core pulsed neutron analysis module, and any combination thereof.

Statement 19: The method of statement 18, wherein the NMR module provides one or more measurements, wherein one or more measurements are relaxation times of Hydrogen nuclei within the at least one rotary core sample, wherein the core imaging analysis module provides one or more measurements, wherein the one or more measurements are x-ray, ultrasonic, resistivity, microstrip resistivity, or any combination thereof measurements of the at least one rotary core sample, and wherein the core pulsed neutron analysis module provides one or more measurements, wherein the one or more measurements are concentrations of Aluminum, Barium, Carbon, Calcium, Chlorine, Iron, Gadolinium, Potassium, Magnesium, Manganese, Sodium, Sulfur, Silicon, or Titanium from the at least one rotary core sample.

Statement 20: The method of any of statements 13-19, further comprising determining a top side of the rotary core sample with the downhole tool.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods may also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any comprised range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A downhole tool comprising:
   a coring module comprising a side drill for obtaining at least one rotary core sample from a formation; and
   a core marker module for marking the at least one rotary core sample with earth coordinates, wherein the coring module is separate from the core marker module.

2. The downhole tool of claim 1, further comprising a friction guide marker for holding the at least one rotary core sample in place within the downhole tool.

3. The downhole tool of claim 2, wherein the friction guide marker comprises a rigid surface.

4. The downhole tool of claim 3, wherein the rigid surface fits within rigid edges of a core tube of the downhole tool.

5. The downhole tool of claim 1, further comprising a core nuclear magnetic resonance module for polarizing Hydrogen nuclei within the rotary core sample.

6. The downhole tool of claim 1, further comprising a core imaging analysis module for imaging the at least one rotary core sample.

7. The downhole tool of claim 1, further comprising a core pulsed neutron analysis module for measuring the at least one rotary core sample.

8. The downhole tool of claim 1, further comprising a core storage module for storing the at least one rotary core sample after marking the at least one rotary core sample with the core marker module.

9. The downhole tool of claim 8, further comprising a motor module that includes a hydraulic line connected to a push rod configured to toggle between retracted and extended positions to move the at least one rotary core sample along a core tube.

10. The downhole tool of claim 1, further comprising one or more sensing modules disposed within the downhole tool, wherein the one or more sensing modules comprises an individual tube that forms part of the core tube that connects at least the coring module and the core marker module.

11. The downhole tool of claim 10, wherein the one or more sensing modules comprise at least one modules selected from the group consisting of a Nuclear Magnetic Resonance module, a core imaging analysis module, and a core pulsed neutron analysis module.

12. A method comprising:
obtaining at least one rotary core sample from a formation with a coring module comprising a side drill within a downhole tool; and
marking the at least one rotary core sample with earth coordinates with a core marker module disposed within the same downhole tool, wherein the core marker module is separate from the coring module.

13. The method of claim 12, further comprising holding the rotary core sample in place within the downhole tool with a friction guide marker.

14. The method of claim 13, wherein the friction guide marker comprises a rigid surface.

15. The method of claim 14, wherein the rigid surface fits within rigid edges of a core tube of the downhole tool.

16. The method of claim 15, wherein a friction coefficient of the rigid edges and/or the rigid surface is based on at least one wellbore environment detail.

17. The method of claim 12, further comprising sensing the at least one rotary core sample with one or more sensing modules disposed within the same downhole tool, wherein the one or more sensing modules are selected from the group consisting of an NMR module, a core imaging analysis module, a core pulsed neutron analysis module, and any combination thereof.

18. The method of claim 17, wherein the NMR module provides one or more measurements, wherein one or more measurements are relaxation times of Hydrogen nuclei within the at least one rotary core sample, wherein the core imaging analysis module provides one or more measurements, wherein the one or more measurements comprises at least one measurement selected from the group consisting of x-ray, ultrasonic, resistivity, microstrip resistivity, or any combination thereof measurements of the at least one rotary core sample, and wherein the core pulsed neutron analysis module provides one or more measurements, wherein the one or more measurements comprises at least one measurer bent selected from the group consisting of concentrations of Aluminum, Barium, Carbon, Calcium, Chlorine, Iron, Gadolinium, Potassium, Magnesium, Manganese, Sodium, Sulfur, Silicon, or Titanium from the at least one rotary core sample.

19. The method of claim 12, further comprising determining a top side of the rotary core sample with the downhole tool.

20. A downhole tool comprising:
a coring module for obtaining at least one rotary core sample from a formation;
a core marker module for marking the at least one rotary core sample with earth coordinates, wherein the coring module is separate from the core marker module;
a core storage module for storing the at least one rotary core sample after marking the at least one rotary core sample with the core marker module; and
a motor module that includes a hydraulic line connected to a push rod configured to toggle between retracted and extended positions to move the at least one rotary core sample along a core tube.

* * * * *